United States Patent
Meyer

(10) Patent No.: US 9,789,088 B2
(45) Date of Patent: *Oct. 17, 2017

(54) METHODS AND COMPOSITIONS FOR DAILY OPHTHALMIC ADMINISTRATION OF PHENTOLAMINE TO IMPROVE VISUAL PERFORMANCE

(71) Applicant: Ocularis Pharma, LLC, North Riverside, IL (US)

(72) Inventor: Alan Meyer, North Riverside, IL (US)

(73) Assignee: Ocularis Pharma, LLC, North Riverside, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/754,965

(22) Filed: Jun. 30, 2015

(65) Prior Publication Data

US 2016/0051515 A1  Feb. 25, 2016

Related U.S. Application Data

(63) Continuation of application No. 14/169,342, filed on Jan. 31, 2014, now Pat. No. 9,089,560.

(60) Provisional application No. 61/759,542, filed on Feb. 1, 2013.

(51) Int. Cl.
| | | |
|---|---|---|
| A61K 31/415 | (2006.01) | |
| A61K 31/417 | (2006.01) | |
| A61K 9/00 | (2006.01) | |
| A61K 47/12 | (2006.01) | |
| A61K 47/26 | (2006.01) | |

(52) U.S. Cl.
CPC .............. *A61K 31/417* (2013.01); *A61K 9/00* (2013.01); *A61K 9/0048* (2013.01); *A61K 47/12* (2013.01); *A61K 47/26* (2013.01)

(58) Field of Classification Search
CPC ...... A61K 31/417; A61K 47/12; A61K 47/26; A61K 9/00; A61K 9/0048
USPC .................................................. 514/401, 912
See application file for complete search history.

(56) References Cited

U.S. PATENT DOCUMENTS

| | | |
|---|---|---|
| 4,443,441 A | 4/1984 | Galin |
| 4,508,715 A | 4/1985 | Booth et al. |
| 4,515,295 A | 5/1985 | Dougherty |
| 4,629,456 A | 12/1986 | Edwards |
| 4,659,714 A | 4/1987 | Watt-Smith |
| 4,834,727 A | 5/1989 | Cope |
| 4,888,344 A | 12/1989 | Sunagawa et al. |
| 4,906,613 A | 3/1990 | Watkins |
| 4,938,970 A | 7/1990 | Hustead et al. |
| 5,059,188 A | 10/1991 | Goddard |
| 5,134,124 A | 7/1992 | Nisato et al. |
| 5,149,320 A | 9/1992 | Dhaliwal et al. |
| 5,192,527 A | 3/1993 | Abrahmsohn |
| 5,261,903 A | 11/1993 | Dhaliwal et al. |
| 5,281,591 A | 1/1994 | Burke |
| 5,288,759 A | 2/1994 | DeSantis, Jr. |
| 5,514,118 A | 5/1996 | Kummer et al. |
| 5,584,823 A | 12/1996 | Valberg |
| 5,591,426 A | 1/1997 | Dabrowski et al. |
| 5,627,611 A | 5/1997 | Scheiner |
| 5,792,767 A | 8/1998 | Meyer et al. |
| 5,885,550 A | 3/1999 | Vallier |
| 5,891,882 A | 4/1999 | Meyer et al. |
| 5,891,913 A | 4/1999 | Sallmann et al. |
| 5,895,654 A | 4/1999 | Hartford et al. |
| 6,001,845 A | 12/1999 | Estok |
| 6,025,396 A | 2/2000 | Kim et al. |
| 6,043,224 A | 3/2000 | Lee et al. |
| 6,046,207 A | 4/2000 | Meyer et al. |
| 6,106,866 A | 8/2000 | Ranney |
| 6,291,498 B1 | 9/2001 | Horn |
| 6,420,407 B1 | 7/2002 | Horn |
| 6,432,401 B2 | 8/2002 | Weber et al. |
| 6,515,006 B2 * | 2/2003 | Horn ................... A61K 31/138 514/369 |
| 6,638,537 B2 | 10/2003 | Dennis et al. |
| 6,730,065 B1 | 5/2004 | Horn |
| 6,730,691 B1 | 5/2004 | Galin |
| 6,764,678 B2 | 7/2004 | Weber et al. |
| 6,872,390 B2 | 3/2005 | Weber et al. |
| 7,229,630 B2 | 6/2007 | Chen et al. |
| 7,569,230 B2 | 8/2009 | Chen et al. |

(Continued)

FOREIGN PATENT DOCUMENTS

| | | |
|---|---|---|
| WO | WO-95/05188 A1 | 2/1995 |
| WO | WO-01/85171 A1 | 11/2001 |
| WO | WO-2005/123093 A2 | 12/2005 |
| WO | WO-2007/008666 A2 | 1/2007 |
| WO | WO-2011/050018 A1 | 4/2011 |
| WO | WO-2011/050030 A1 | 4/2011 |
| WO | WO-2012/075319 A2 | 6/2012 |
| WO | WO-2012/112566 A1 | 8/2012 |
| WO | WO-2012/119059 A1 | 9/2012 |
| WO | WO-2012/119070 A2 | 9/2012 |

(Continued)

OTHER PUBLICATIONS

Murphy et al., "How red is a white eye? Clinical grading of normal conjunctival hyperaemia", May 2007, Eye, 21(5), pp. 633-638.*

(Continued)

*Primary Examiner* — My-Chau T Tran
(74) *Attorney, Agent, or Firm* — Goodwin Procter LLP

(57) ABSTRACT

The invention provides methods, compositions, and kits containing phentolamine for improving visual performance. In particular, the invention provides improvement in visual performance, such as improvement in visual acuity, by daily ophthalmic administration of a phentolamine solution to an eye of a patient at or near the bedtime of the patient for an extended duration while minimizing the occurrence of adverse side effects, such as eye redness during the patient's waking hours.

26 Claims, 13 Drawing Sheets

(56) References Cited

U.S. PATENT DOCUMENTS

| | | | |
|---|---|---|---|
| 7,575,757 | B2 | 8/2009 | Chen et al. |
| 7,868,035 | B2 | 1/2011 | Woodward et al. |
| 8,445,526 | B2 | 5/2013 | Horn |
| 8,580,787 | B2 | 11/2013 | Horn |
| 8,597,629 | B1 | 12/2013 | Horn |
| 8,889,112 | B2 | 11/2014 | Horn |
| 8,979,809 | B2 * | 3/2015 | Horn ............... A61K 31/00 424/78.04 |
| 9,089,560 | B2 * | 7/2015 | Meyer ............... A61K 9/00 |
| 2002/0082288 | A1 | 6/2002 | Horn |
| 2002/0183356 | A1 | 12/2002 | Weber et al. |
| 2002/0183396 | A1 | 12/2002 | Weber et al. |
| 2002/0187986 | A1 | 12/2002 | Horn |
| 2003/0236306 | A1 | 12/2003 | Chen et al. |
| 2004/0053894 | A1 | 3/2004 | Mazess et al. |
| 2004/0176408 | A1 | 9/2004 | Horn |
| 2005/0080056 | A1 | 4/2005 | Horn |
| 2005/0203099 | A1 | 9/2005 | Chen et al. |
| 2006/0211753 | A1 | 9/2006 | Horn |
| 2006/0257388 | A1 | 11/2006 | Knowles |
| 2007/0098748 | A1 | 5/2007 | Chen et al. |
| 2009/0220618 | A1 | 9/2009 | Xia et al. |
| 2009/0232763 | A1 | 9/2009 | Kabra et al. |
| 2010/0029663 | A1 * | 2/2010 | Horn ............... A61K 9/08 514/249 |
| 2010/0324031 | A1 | 12/2010 | Kabra |
| 2011/0178147 | A1 | 7/2011 | Likitlersuang et al. |
| 2012/0149748 | A1 | 6/2012 | Shanler et al. |
| 2012/0208858 | A1 | 8/2012 | Shanler et al. |
| 2012/0238615 | A1 | 9/2012 | Chow et al. |
| 2012/0277239 | A1 | 11/2012 | Horn et al. |
| 2013/0029919 | A1 | 1/2013 | Gore et al. |
| 2013/0143938 | A1 | 6/2013 | Horn |
| 2013/0172357 | A1 | 7/2013 | Horn |
| 2014/0221445 | A1 * | 8/2014 | Meyer ............... A61K 31/417 514/401 |
| 2014/0221446 | A1 | 8/2014 | Meyer |

FOREIGN PATENT DOCUMENTS

| | | |
|---|---|---|
| WO | WO-2013/115844 A1 | 8/2013 |
| WO | WO-2013/130577 A2 | 9/2013 |

OTHER PUBLICATIONS

National Institutes of Health, "Visual acuity test", Feb. 23, 2015, online: //medlineplus.gov/ency/article/003396.htm, 3 pages total.*

Abad et al., "Comparison of Astigmatism Correction Using Shorter Arc Length 90° / 120° Asymmetric Intacs Severe Keratoconus Versus 150° Single-Segment Intacs Severe Keratoconus in Asymmetric Keratoconus," Cornea, (2011), vol. 30, No. 11, pp. 1201-1206.

Benson et al., "Is Phentolamine Stable in Solution with Papaverine," The Journal of Urology, (1988), vol. 140, pp. 970-971.

Hadzija et al., "Physicochemical Stability of Papaverine Hydrochloride-Phentolamine Mesylate Mixtures Used for Intracavernous Injection: A Preliminary Evaluation," The Journal of Urology, (1988), vol. 140, pp. 64-65.

International Search Report and Written Opinion of the International Searching Authority, the U.S. Patent & Trademark Office, for International Application No. PCT/US2014/014067, dated May 21, 2014, 8 pages.

International Search Report and Written Opinion of the International Searching Authority, the U.S. Patent & Trademark Office, for International Application No. PCT/US2014/014070, dated Apr. 15, 2014, 10 pages.

OraVerse (phentolamine mesylate) Injection, Prescribing Information, 2 pages.

Soli et al., "Vasoactive Cocktails for Erectile Dysfunction: Chemical Stability of PGE1, Papaverine and Phentolamine," The Journal of Urology, (1998), vol. 160, pp. 551-555.

Tu et al., "Stability of papaverine hydrochloride and phentolamine mesylate in injectable mixtures," American Journal of Hospital Pharmacy, (1987), vol. 44, pp. 2524-2527.

Wang et al., "Degradation Kinetics of Phentolamine Hydrochloride in Solution," Journal of Pharmaceutical Sciences, (1988), Vo. 77, No. 11, pp. 972-976.

Martell, A.E., "Chelates of Ascorbic Acid Formation and Catalytic Properties," Advances in Chemistry, vol. 200, pp. 153-178 (1982).

Abelson, M. B. and Vashlishan, A. "The Truth About Tachyphylaxis," Review of Ophthalmology, (2006), vol. 13, No. 3, pp. 112-115.

Johnston, C. "Relief for Patients Troubled by Night-Vision Complaints: Presented at AAO". PeerVoice publication, dated Oct. 21, 2010.

* cited by examiner

METHODS AND COMPOSITIONS FOR DAILY OPHTHALMIC ADMINISTRATION OF PHENTOLAMINE TO IMPROVE VISUAL PERFORMANCE

RELATED APPLICATIONS

This application is a continuation of U.S. patent application Ser. No. 14/169,342, filed Jan. 31, 2014, which claims the benefit of and priority to U.S. Provisional Patent Application Ser. No. 61/759,542, filed Feb. 1, 2013, the entire contents of each application are incorporated herein by reference in their entirety.

FIELD OF THE INVENTION

The invention provides methods, compositions, and kits containing phentolamine for improving visual performance. In particular, the invention provides improvement in visual performance, such as improvement in visual acuity, by daily ophthalmic administration of a phentolamine solution to an eye of a patient at or near the bedtime of the patient for an extended duration while minimizing the occurrence of adverse side effects, such as eye redness during the patient's waking hours.

BACKGROUND

Deficient visual performance can have a significant negative impact on a patient's quality of life, affecting, for example, ability to perform normal daily tasks, perform at school, and perform at work. The inability to see clearly can impact people during normal daylight conditions and during low-light conditions, such as nighttime. One type of vision problem experienced by a substantial number of patients is poor night vision. The inability to see clearly under such low light conditions can make it difficult and/or dangerous for a patient to operate a motor vehicle at nighttime. Patients that are more likely to experience night vision problems include those suffering from night myopia, have an equatorial cortical cataract, have had surgery to insert an intraocular lens, and/or underwent LASIK surgery. Exemplary symptoms of poor night vision include glare, halos, starburst, ghosting patterns, and/or poor depth perception.

Certain therapies have been described for improving visual performance. For example, the Bernstein Center for Visual Performance offers programs that utilize visual aids, such as puzzles, stereoscopes, and eye glasses, designed to improve visual performance. U.S. Pat. No. 6,291,498 describes the use of phentolamine to, for example, optimize pupil size in a patient. However, one adverse side effect of phentolamine administered to the eye of a patient is eye redness. The need exists for methods and compositions that provide the patient with improved visual performance during the patient's waking hours, while minimizing the occurrence and/or degree of eye redness caused by phentolamine during the patient's waking hours.

The present invention addresses the aforementioned need for methods and compositions for achieving improved visual performance while minimizing the occurrence and/or degree of eye redness caused by phentolamine during the patient's waking hours, and the invention provides other related advantages.

SUMMARY

The invention provides methods, compositions, and kits containing phentolamine for improving visual performance. One aspect of the invention provides improvement in visual performance, such as improvement in visual acuity, by daily ophthalmic administration of a phentolamine solution to an eye of a patient at or near the bedtime of the patient for an extended duration while minimizing the occurrence of adverse side effects, such as eye redness during the patient's waking hours. The methods and compositions provide particular benefits to patients suffering from reduced visual performance during normal daylight conditions and during low light conditions, such as nighttime. One benefit of administering the ophthalmic solution at bedtime is that the patient desirably will not experience any significant eye redness during waking hours. Another benefit provided by the invention is that improved visual performance is achieved without diminution in efficacy of the phentolamine solution even after daily administration for an extended period of time. Exemplary aspects and embodiments of the invention are described below.

Another aspect of the invention provides a method of improving visual performance in a patient while minimizing eye redness during the patient's waking hours. The method comprises administering to an eye of a patient once per day at or near the bedtime of the patient for at least five consecutive days a daily dosage of phentolamine or a pharmaceutically acceptable salt thereof sufficient to provide improved visual performance for at least twenty hours, wherein the patient experiences an increase in eye redness of no more than two grades measured using the CCLRU Redness Grading Scale during the patient's waking hours compared to the patient's level of eye redness without receiving said dosage. Eye redness is an undesirable side effect experienced by certain patients when phentolamine is administered to the eye. The present invention provides improvement in visual performance during the patient's waking hours, while minimizing eye redness experienced by the patient during the patient's waking hours.

Another aspect of the invention provides a method of reducing pupil diameter in a patient while minimizing eye redness during the patient's waking hours. The method comprises administering to an eye of a patient once per day at or near the bedtime of the patient for at least five consecutive days a daily dosage of phentolamine or a pharmaceutically acceptable salt thereof sufficient to reduce pupil diameter for at least twenty hours, wherein the patient experiences an increase in eye redness of no more than two grades measured using the CCLRU Redness Grading Scale during the patient's waking hours compared to the patient's level of eye redness without receiving said dosage. Reduction in pupil diameter is contemplated to provide improvements in visual performance.

Another aspect of the invention provides a method of reducing an aberrant focus of scattered light rays in a patient's eye while minimizing eye redness during the patient's waking hours. The method comprises administering to an eye of a patient once per day at or near the bedtime of the patient for at least five consecutive days a daily dosage of phentolamine or a pharmaceutically acceptable salt thereof sufficient to reduce aberrant focus of scattered light rays in a patient's eye for at least twenty hours, wherein the patient experiences an increase in eye redness of no more than two grades measured using the CCLRU Redness Grading Scale during the patient's waking hours compared to the patient's level of eye redness without receiving said dosage. The reduction in aberrant focus of scattered light rays in a patient's eye is contemplated to provide an improvement in visual performance.

DETAILED DESCRIPTION OF THE INVENTION

Figure 1:
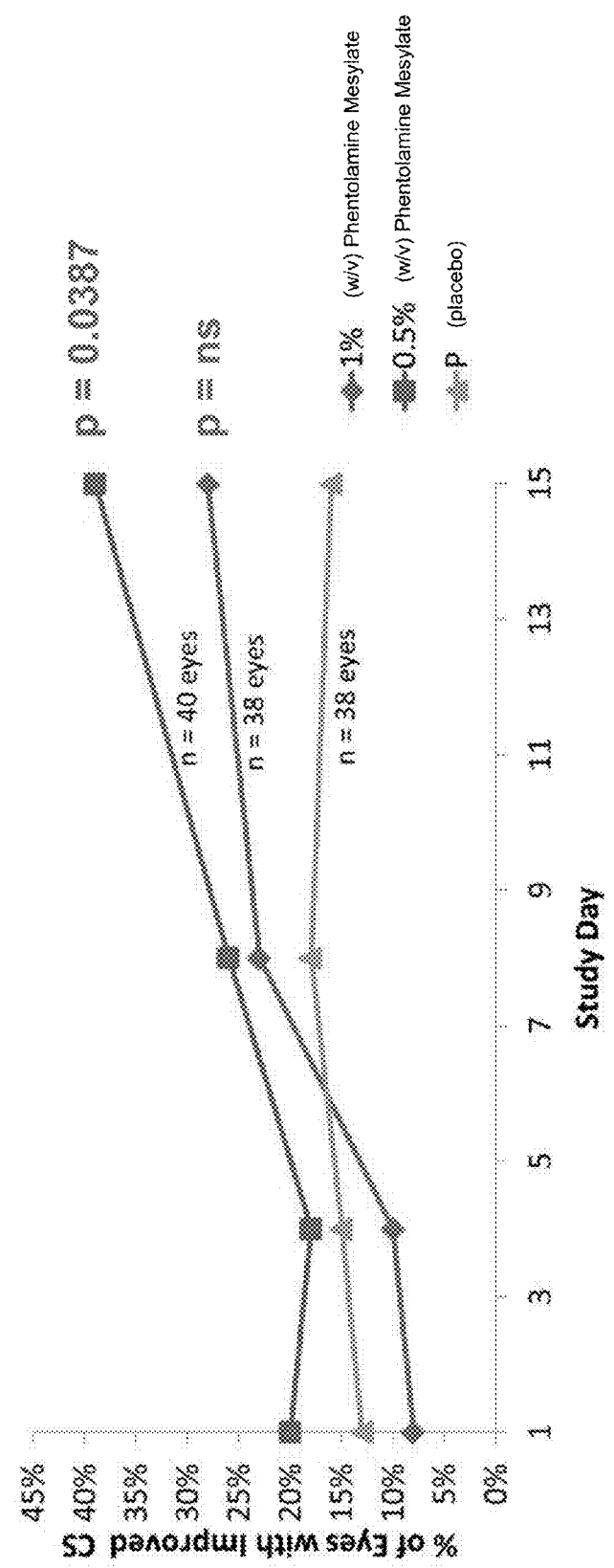
FIG. 1 is a line graph showing the percentage of eyes that showed at least a 50% improvement in contrast sensitivity relative to baseline following daily administration of phentolamine mesylate, as described in Example 1 where the patient's contrast sensitivity was measured on days 1, 4, 8, and 15 of the study two hours after administration of that day's dose.

The invention provides methods, compositions, and kits containing phentolamine for improving visual performance. One benefit of the invention is that it provides improvement in visual performance, such as improvement in visual acuity, during the patient's waking hours while minimizing the occurrence of adverse side effects, such as eye redness during the patient's waking hours. Another benefit is that the invention provides improved visual performance without diminution in efficacy of the phentolamine solution even after daily administration for an extended period of time. The methods and compositions provide particular benefits to patients suffering from poor visual performance during normal light conditions and during low light conditions, such as nighttime. Various aspects of the invention are set forth below in sections; however, aspects of the invention described in one particular section are not to be limited to any particular section.

Definitions

To facilitate an understanding of the present invention, a number of terms and phrases are defined below.

The terms "a," "an" and "the" as used herein mean "one or more" and include the plural unless the context is inappropriate As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. Unless specified otherwise, an effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin in Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate (mesylate), 2-naphthalenesulfonate, nicotinate, oxalate, palmoate, pectinate, persulfate, phenylpropionate, picrate, pivalate, propionate, succinate, sulfate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "alkanoate" is art-recognized and refers to alkyl-$C(O)O^-$.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Therapeutic Methods

The invention provides methods for improving visual performance, reducing pupil diameter, and reducing an aberrant focus of scattered light rays in a patient's eye. The methods involve daily ophthalmic administration of a phentolamine solution to an eye of a patient at or near the bedtime of the patient. The daily ophthalmic administration of a phentolamine solution is repeated for an extended duration, such as for at least about five or seven consecutive days. Various aspects and embodiments of the therapeutic methods are described in the sections below. The sections are arranged for convenience and information in one section is not to be limited to that section, but may be applied to methods in other sections.

A. Methods for Improving Visual Performance

One aspect of the invention provides a method of improving visual performance in a patient while minimizing eye redness during the patient's waking hours. The method comprises administering to an eye of a patient once per day at or near the bedtime of the patient for at least five consecutive days a daily dosage of phentolamine or a pharmaceutically acceptable salt thereof sufficient to provide improved visual performance for at least twenty hours, wherein the patient experiences an increase in eye redness of no more than two grades measured using the CCLRU Redness Grading Scale during the patient's waking hours compared to the patient's level of eye redness without receiving said dosage.

Visual performance pertains to the patient's overall vision quality and includes a patient's ability to see clearly, as well as ability to distinguish between an object and its background. One aspect of visual performance is visual acuity. Visual acuity is a measure of a patient's ability to see clearly. Visual acuity can be measured using, for example, a Snellen chart. Further, the visual acuity measurement can be taken under scotopic conditions, mesopic conditions, and/or photopic conditions. Another aspect of visual performance is contrast sensitivity. Contrast sensitivity is a measure of the patient's ability to distinguish between an object and its background. Contrast sensitivity can be measured using, for example, a Holladay Automated Contrast Sensitivity System. The contrast sensitivity can be measured under various light conditions, including, for example, photopic conditions, mesopic conditions, and scotopic conditions, each either with or without glare. In certain embodiments, the contrast sensitivity is measured under mesopic conditions either with or without glare.

In certain embodiments, the improvement in visual performance provided by the method is improved visual acuity. In certain embodiments, the improvement in visual performance provided by the method is improved visual acuity under scotopic conditions. In certain embodiments, the improvement in visual performance provided by the method is improved visual acuity under mesopic conditions. In certain embodiments, the improvement in visual performance provided by the method is improved visual acuity under photopic conditions. In certain embodiments, the improvement in visual acuity is a two-line improvement in the patient's vision as measured using the Snellen chart. In certain other embodiments, the improvement in visual acuity is a one-line improvement in the patient's vision as measured using the Snellen chart.

In certain embodiments, the improvement in visual performance provided by the method is improved contrast sensitivity. The improvement in contrast sensitivity can be measured under various light conditions, such as photopic conditions, mesopic conditions, and scotopic conditions. In certain embodiments, the improvement in visual performance provided by the method is improved contrast sensitivity under photopic conditions. In certain embodiments, the improvement in visual performance provided by the method is improved contrast sensitivity under mesopic conditions. In certain embodiments, the improvement in visual performance provided by the method is improved contrast sensitivity under scotopic conditions. Further, contrast sensitivity can be measured in the presence of glare or the absence of glare. All combinations of light conditions and glare are contemplated.

Results achieved by the therapeutic methods can be characterized according to the patient's improvement in contrast sensitivity. For example, in certain embodiments, the improvement in contrast sensitivity is at least a 10% (or 20%, 30%, 50%, 60%, or 70%) improvement measured under mesopic conditions using the Holladay Automated Contrast Sensitivity System. In certain embodiments, the improvement in contrast sensitivity is at least a 10% (or 20%, 30%, 50%, 60%, or 70%) improvement measured under photopic conditions using the Holladay Automated Contrast Sensitivity System. In certain other embodiments, the improvement in contrast sensitivity is at least a 10% (or 20%, 30%, 50%, 60%, or 70%) improvement measured under mesopic conditions or scotopic conditions using the Holladay Automated Contrast Sensitivity System.

In certain other embodiments, the improvement in visual performance provided by the method is both (i) improved visual acuity (such as under scotopic conditions, mesopic conditions, and/or photopic conditions) and (ii) improved contrast sensitivity (such as under scotopic conditions, mesopic conditions, and/or photopic conditions).

Figure 11:
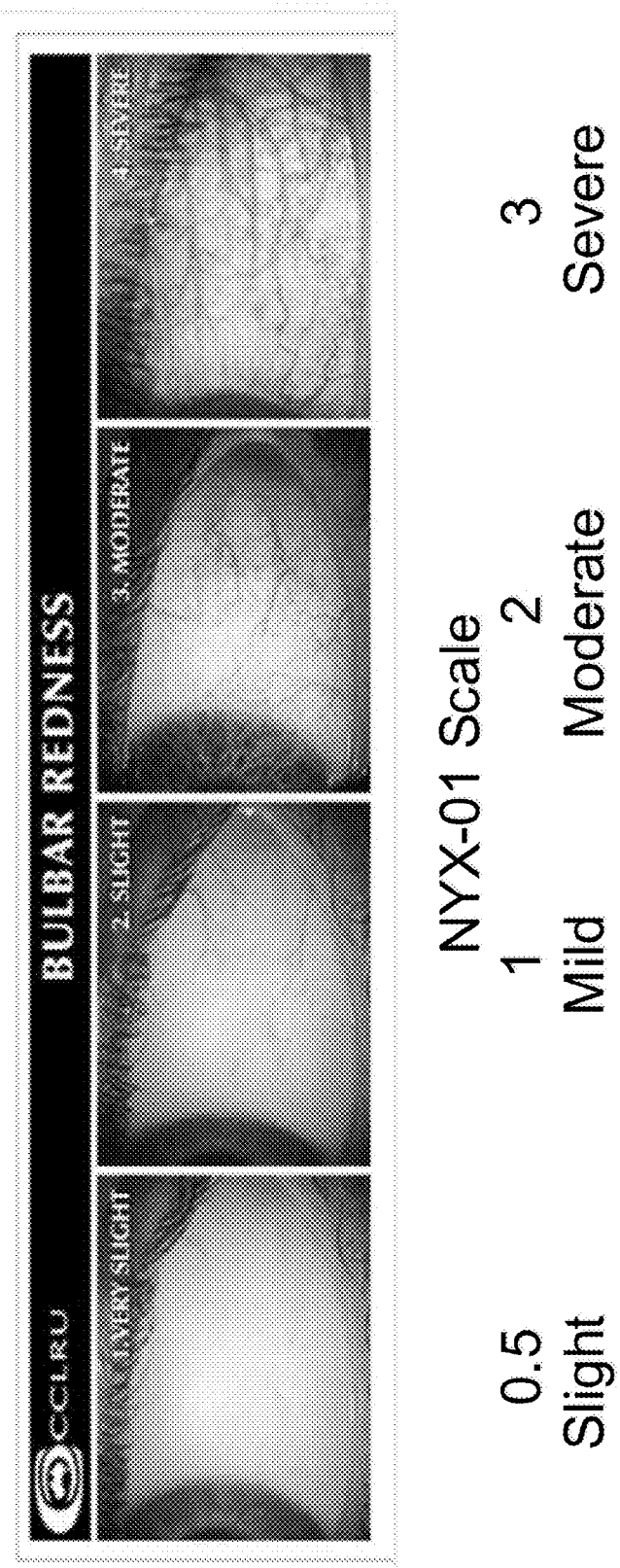
FIG. 11 depicts exemplary eye redness as measured according to (1) the CCLRU Redness Grading Scale, and (2) the NYX-001 Redness Grading Scale used in Example 1.

The degree of eye redness can be evaluated and characterized using procedures described in the literature, such as the Cornea and Contact Lens Research Unit (CCLRU) Redness Grading Scale developed by the School of Optometry, University of New South Wales. See, for example, Terry et al. in *Optom. Vis. Sci.* (1993) vol. 70, pages 234-243; and Pult et al. in *Ophthal. Physiol. Opt.* (2008) vol. 28, pages 13-20. The CCLRU Redness Grading Scale evaluates eye redness on a four-point scale: (0) no eye redness, (1) very slight eye redness, (2) slight eye redness, (3) moderate eye redness, and (4) severe eye redness. See FIG. 11 for an illustration of the eye redness scale.

In certain embodiments, the patient experiences an increase in eye redness of no more than one grade measured using the CCLRU Redness Grading Scale during the patient's waking hours compared to the patient's level of eye redness without receiving said dosage.

The daily dosage of phentolamine or a pharmaceutically acceptable salt thereof can be administered for greater than five consecutive days. For example, in certain embodiments, the daily dosage of phentolamine or a pharmaceutically acceptable salt thereof is administered for at least seven consecutive days. In yet other embodiments, the daily dosage of phentolamine or a pharmaceutically acceptable salt thereof is administered for at least 10, 15, 20, 30, 60, 90, or 120 consecutive days, or even a larger number of consecutive days. One benefit of the invention is that the phentolamine or a pharmaceutically acceptable salt thereof can be used on a chronic basis, that is the dosage can be administered daily for a large number of consecutive days. Eye redness associated with administration of phentolamine or a pharmaceutically acceptable salt thereof did not worsen with consecutive daily administration of phentolamine or a pharmaceutically acceptable salt, and no diminution in efficacy of the phentolamine solution was observed after daily administration for an extended period of time. Exemplary durations of chronic use include, for example, daily use over a period of about 4, 5, 6, 7, 8, 9, 10, 11, or 12 months or longer.

The amount of phentolamine or a pharmaceutically acceptable salt thereof in the daily dosage is sufficient to provide improved visual performance for at least twenty hours. In certain embodiments, the amount of phentolamine or a pharmaceutically acceptable salt thereof in the daily dosage is sufficient to provide improved visual performance for at least twenty-four hours. In yet other embodiments, the amount of phentolamine or a pharmaceutically acceptable salt thereof in the daily dosage is sufficient to provide improved visual performance for at least thirty-six hours, forty-eight hours, sixty hours, or seventy-two hours. In still other embodiments, the amount of phentolamine or a pharmaceutically acceptable salt thereof in the daily dosage is sufficient to provide improved visual performance for at least 4, 5, 6, 7, 8, 9, 10, or 11 days. In certain embodiments, the daily dosage is about one eye drop per eye of an ophthalmic solution comprising from about 0.1% (w/v) to about 2.0% (w/v) phentolamine mesylate. In certain other embodiments, the daily dosage is about one eye drop per eye of an ophthalmic solution comprising from about 0.25% (w/v) to about 1.0% (w/v) phentolamine mesylate, or from about 0.5% (w/v) to about 1.0% (w/v) phentolamine mesylate.

B. Methods for Reducing Pupil Diameter

Another aspect of the invention provides methods for reducing pupil diameter in a patient while minimizing eye redness during the patient's waking hours. The method comprises administering to an eye of a patient once per day at or near the bedtime of the patient for at least five consecutive days a daily dosage of phentolamine or a pharmaceutically acceptable salt thereof sufficient to reduce pupil diameter for at least twenty hours, wherein the patient experiences an increase in eye redness of no more than two grades measured using the CCLRU Redness Grading Scale during the patient's waking hours compared to the patient's level of eye redness without receiving said dosage. The reduction in pupil diameter is understood to provide improvements in visual performance for the patient.

The reduction in pupil diameter can be characterized according to, for example, the percent reduction in pupil diameter and size of the pupil measured under certain light conditions. Accordingly, in certain embodiments, the reduction in pupil diameter under mesopic conditions is at least 5% compared to the pupil diameter of the patient under the same mesopic conditions but not having received the aqueous ophthalmic solution. In certain other embodiments, the reduction in pupil diameter under mesopic conditions is at least 10% compared to the pupil diameter of the patient under the same mesopic conditions but not having received the aqueous ophthalmic solution. In certain other embodiments, the patient experiences a reduction in pupil diameter of at least 0.5 mm when measured under mesopic conditions relative to the diameter of the patient's pupil under the same mesopic conditions but not having received the aqueous ophthalmic solution. In certain other embodiments, the patient experiences a reduction in pupil diameter ranging from about 0.6 mm to about 3 mm, about 0.6 mm to about 2.5 mm, or about 0.6 mm to about 2 mm when measured under mesopic conditions relative to the diameter of the patient's pupil under the same mesopic conditions but not having received the aqueous ophthalmic solution. In certain other embodiments, the patient experiences a reduction in pupil diameter ranging from about 0.6 mm to about 1.2 mm when measured under mesopic conditions relative to the diameter of the patient's pupil under the same mesopic conditions but not having received the aqueous ophthalmic solution. In yet other embodiments, the patient's pupil is reduced to a diameter of about 3 mm to about 5 mm, about 3 mm to about 6 mm, about 4 mm to about 5 mm, about 4 mm to about 6 mm, or about 4 mm to about 7 mm under mesopic conditions due to the aqueous ophthalmic solution.

In certain embodiments, the patient's pupil is reduced to a diameter of about 4 mm to about 6 mm under mesopic conditions due to the aqueous ophthalmic solution.

In certain other embodiments, the reduction in pupil diameter under scotopic conditions is at least 5% compared to the pupil diameter of the patient under the same scotopic conditions but not having received the aqueous ophthalmic solution. In certain other embodiments, the reduction in pupil diameter under scotopic conditions is at least 10% compared to the pupil diameter of the patient under the same scotopic conditions but not having received the aqueous ophthalmic solution. In certain other embodiments, the patient experiences a reduction in pupil diameter of at least 0.5 mm when measured under scotopic conditions relative to the diameter of the patient's pupil under the same scotopic conditions but not having received the aqueous ophthalmic solution. In certain other embodiments, the patient experiences a reduction in pupil diameter ranging from about 0.6 mm to about 3 mm, about 0.6 mm to about 2.5 mm, or about 0.6 mm to about 2 mm when measured under scotopic conditions relative to the diameter of the patient's pupil under the same scotopic conditions but not having received the aqueous ophthalmic solution. In certain other embodiments, the patient experiences a reduction in pupil diameter ranging from about 0.6 mm to about 1.2 mm when measured under scotopic conditions relative to the diameter of the patient's pupil under the same scotopic conditions but not having received the aqueous ophthalmic solution. In yet other embodiments, the patient's pupil is reduced to a diameter of about 3 mm to about 5 mm, about 3 mm to about 6 mm, about 4 mm to about 5 mm, about 4 mm to about 6 mm, or about 4 mm to about 7 mm under scotopic conditions due to the aqueous ophthalmic solution. In certain embodiments, the patient's pupil is reduced to a diameter of about 4 mm to about 6 mm under scotopic conditions due to the aqueous ophthalmic solution.

The daily dosage of phentolamine or a pharmaceutically acceptable salt thereof can be administered for greater than five consecutive days. For example, in certain embodiments, the daily dosage of phentolamine or a pharmaceutically acceptable salt thereof is administered for at least seven consecutive days. In yet other embodiments, the daily dosage of phentolamine or a pharmaceutically acceptable salt thereof is administered for at least 10, 15, or 20 consecutive days or longer. One benefit of the invention is that the phentolamine or a pharmaceutically acceptable salt thereof can be used on a chronic basis, that is the dosage can be administered daily for a large number of consecutive days. Eye redness associated with administration of phentolamine or a pharmaceutically acceptable salt thereof did not worsen with consecutive daily administration of phentolamine or a pharmaceutically acceptable salt, and no diminution in efficacy of the phentolamine solution was observed after daily administration for an extended period of time. Exemplary durations of chronic use include, for example, daily use over a period of about 4, 5, 6, 7, 8, 9, 10, 11, or 12 months or longer.

The amount of phentolamine or a pharmaceutically acceptable salt thereof in the daily dosage is sufficient to reduce pupil diameter for at least twenty hours. In certain embodiments, the amount of phentolamine or a pharmaceutically acceptable salt thereof in the daily dosage is sufficient to reduce pupil diameter for at least twenty-four hours. In yet other embodiments, the amount of phentolamine or a pharmaceutically acceptable salt thereof in the daily dosage is sufficient to reduce pupil diameter for at least thirty-six hours, forty-eight hours, sixty hours, or seventy-two hours.

In still other embodiments, the amount of phentolamine or a pharmaceutically acceptable salt thereof in the daily dosage is sufficient to reduce pupil diameter for at least 4, 5, 6, 7, 8, 9, 10, or 11 days. In certain embodiments, the daily dosage is about one eye drop per eye of an ophthalmic solution comprising from about 0.5% (w/v) to about 1.0% (w/v) phentolamine mesylate. In certain other embodiments, the daily dosage is about one eye drop per eye of an ophthalmic solution comprising from about 0.25% (w/v) to about 1.0% (w/v) phentolamine mesylate.

In certain embodiments, the patient experiences an increase in eye redness of no more than one grade measured using the CCLRU Redness Grading Scale during the patient's waking hours compared to the patient's level of eye redness without receiving said dosage.

C. Methods for Reducing Aberrant Focus of Scattered Light Rays in a Patient's Eye Another benefit of the therapies described herein is that they can improve visual performance in a patient by reducing the aberrant focus of scattered light rays in the patient's eye. Accordingly, one aspect of the invention provides a method of reducing an aberrant focus of scattered light rays in a patient's eye while minimizing eye redness during the patient's waking hours. The method comprises administering to an eye of a patient once per day at or near the bedtime of the patient for at least five consecutive days a daily dosage of phentolamine or a pharmaceutically acceptable salt thereof sufficient to reduce aberrant focus of scattered light rays in a patient's eye for at least twenty hours, wherein the patient experiences an increase in eye redness of no more than two grades measured using the CCLRU Redness Grading Scale during the patient's waking hours compared to the patient's level of eye redness without receiving said dosage.

In certain embodiments, the patient experiences an increase in eye redness of no more than one grade measured using the CCLRU Redness Grading Scale during the patient's waking hours compared to the patient's level of eye redness without receiving said dosage.

The daily dosage of phentolamine or a pharmaceutically acceptable salt thereof can be administered for greater than five consecutive days. For example, in certain embodiments, the daily dosage of phentolamine or a pharmaceutically acceptable salt thereof is administered for at least seven consecutive days. In yet other embodiments, the daily dosage of phentolamine or a pharmaceutically acceptable salt thereof is administered for at least 10, 15, or 20 consecutive days or longer. One benefit of the invention is that the phentolamine or a pharmaceutically acceptable salt thereof can be used on a chronic basis, that is the dosage can be administered daily for a large number of consecutive days. Eye redness associated with administration of phentolamine or a pharmaceutically acceptable salt thereof did not worsen with consecutive daily administration of phentolamine or a pharmaceutically acceptable salt, and no diminution in efficacy of the phentolamine solution was observed after daily administration for an extended period of time. Exemplary durations of chronic use include, for example, daily use over a period of about 4, 5, 6, 7, 8, 9, 10, 11, or 12 months or longer.

The amount of phentolamine or a pharmaceutically acceptable salt thereof in the daily dosage is sufficient to reduce aberrant focus of scattered light rays in a patient's eye for at least twenty hours. In certain embodiments, the amount of phentolamine or a pharmaceutically acceptable salt thereof in the daily dosage is sufficient reduce aberrant focus of scattered light rays in a patient's eye for at least twenty-four hours. In yet other embodiments, the amount of phentolamine or a pharmaceutically acceptable salt thereof in the daily dosage is sufficient to reduce aberrant focus of scattered light rays in a patient's eye for at least thirty-six hours, forty-eight hours, sixty hours, or seventy-two hours. In certain embodiments, the daily dosage is about one eye drop per eye of an ophthalmic solution comprising from about 0.5% (w/v) to about 1.0% (w/v) phentolamine mesylate. In certain other embodiments, the daily dosage is about one eye drop per eye of an ophthalmic solution comprising from about 0.25% (w/v) to about 1.0% (w/v) phentolamine mesylate.

D. General Considerations for Therapeutic Methods

General considerations that may be applied to therapeutic methods described herein (e.g., the methods described in Parts A-C above) are provided below and include, for example, the form of the daily dosage, time of day when the daily dosage is administered, additional procedures for evaluating improvement in visual performance, and patient populations that may derive particular benefits from the therapeutic methods.

The daily dosage of phentolamine or a pharmaceutically acceptable salt thereof is desirably administered to the eye of the patient in the form of an ophthalmic solution, which is delivered to the eye in the form of eye drop. A standard eye drop typically contains from about 0.03 mL to about 0.05 mL of solution.

Various methods described above require administration of the daily dosage at or near the bedtime of the patient. Accordingly, in certain embodiments, the daily dosage is administered within 2 hours, 1.5 hours, 1 hour, 45 minutes, 30 minutes, or 15 minutes of patient's bedtime. In certain embodiments, the daily dosage is administered within 1 hour of the patient's bedtime.

The methods can be further characterized according to improvement in visual acuity measured using a Snellen chart. For example, in certain embodiments, the method results in an improvement in visual acuity characterized by at least a one-line improvement in the patient's vision measured using a Snellen chart. In certain other embodiments, the method results in an improvement in visual acuity characterized by at least a two-line improvement in the patient's vision measured using a Snellen chart. The improvement in visual acuity can be measured under photopic conditions, mesopic conditions, and/or scotopic conditions. Further, the visual acuity measurement can be taken under conditions that test low-contrast visual acuity or under conditions that test high-contrast visual acuity.

Certain patient populations may respond particularly well to the therapeutic methods. One way to characterize patients is according to eye color, such as those having a substantial amount of pigment in their iris. As such, one population of patients is those in which the patient's iris is brown. Another way to characterize patient populations is according to race, such as African American, Hispanic, and Asian patients.

It is reiterated here that all embodiments described throughout the patent application (including, for example, Sections A-C) may be combined in various permutations and all such permutations are contemplated. For example, it is contemplated that the method of providing improvement in visual performance in a patient described in Section A may be further characterized according to, for example, (i) changes in pupil diameter described in Section C and/or (ii) administering the ophthalmic solution within one hour of the patient's bedtime as described in Section D. Likewise, the methods in Sections B-D can be characterized according to embodiments described in Section A, such as those pertaining to threshold improvements in visual performance, such as where (i) the method results in at least at least a 10% (or 20%, 30%, 50%, 60%, or 70%) improvement in contrast sensitivity measured under mesopic conditions using the Holladay Automated Contrast Sensitivity System.

II. Ophthalmic Solutions Containing Phentolamine

The therapeutic methods involve administering a daily dosage of phentolamine or a pharmaceutically acceptable salt thereof to the patient. The daily dosage of phentolamine or a pharmaceutically acceptable salt thereof is desirably in the form of an ophthalmic solution. The ophthalmic solution is formulated to be suitable for administration to the eye of a patient, and desirably provides immediate release of phentolamine, that is, the ophthalmic solution is not a sustained release formulation that delivers phentolamine over an extended duration, such as hours, days or weeks.

The ophthalmic solution desirably comprises an aqueous pharmaceutically acceptable carrier and phentolamine or a pharmaceutically acceptable salt thereof. The ophthalmic solution may contain excipients(s) that are suitable for administration to the eye. Various pharmaceutically acceptable salts are described in the literature. The preferred salt form of phentolamine is phentolamine mesylate. Accordingly, the methods may use an ophthalmic solution that comprises an aqueous pharmaceutically acceptable carrier and phentolamine mesylate.

Accordingly, in certain embodiments, the daily dosage utilized in the methods is an ophthalmic solution comprising an aqueous pharmaceutically acceptable carrier and phentolamine or a pharmaceutically acceptable salt thereof. In certain other embodiments, the daily dosage is an ophthalmic solution comprising an aqueous pharmaceutically acceptable carrier and phentolamine mesylate. In certain other embodiments, the daily dosage is an ophthalmic solution comprising water, a polyol, and phentolamine or a pharmaceutically acceptable salt thereof. In certain other embodiments, the daily dosage is an ophthalmic solution comprising water, mannitol, and phentolamine mesylate. In certain other embodiments, the daily dosage is an ophthalmic solution comprising water, a polyol, an alkali metal carboxylate, and phentolamine or a pharmaceutically acceptable salt thereof. In certain other embodiments, the daily dosage is an ophthalmic solution comprising water, mannitol, sodium acetate, and phentolamine mesylate.

Other ophthalmic solutions that are contemplated for use in the present invention include, for example, (i) aqueous ophthalmic solutions free of a chelating agent, and (ii) polyvinylpyrrolidone artificial tears formulations, each of which are described in more detail below.

Aqueous Ophthalmic Solution Free of a Chelating Agent

In certain embodiments, the daily dosage utilized in the methods is an aqueous ophthalmic solution free of a chelating agent, wherein said solution comprises (a) phentolamine or a pharmaceutically acceptable salt thereof; (b) at least one polyol compound, such as a polyol compound having a molecular weight less than 250 g/mol; (c) at least one buffer; and (d) water; wherein the solution does not contain a chelating agent. The amount of ingredients in the aqueous ophthalmic solutions may be selected in order to achieve particular performance properties, such as stability to storage, minimize irritation to the eye of a patient, and enhance penetration of phentolamine into the eye of a patient.

One exemplary preferred solution is an aqueous ophthalmic solution free of a chelating agent comprising: (a) about 0.1% (w/v) to about 4% (w/v) of phentolamine or a pharmaceutically acceptable salt thereof; (b) about 1% (w/v) to about 6% (w/v) of at least one polyol compound having a molecular weight less than 250 g/mol; (c) about 0.1 mM to about 10 mM of at least one buffer; and (d) water; wherein the solution has a pH in the range of 4.0 to 7.5 and does not contain a chelating agent.

Exemplary components and features of the aqueous ophthalmic solutions are described in more detail below.

Phentolamine & Pharmaceutically Acceptable Salts

The aqueous ophthalmic solution comprises phentolamine or a pharmaceutically acceptable salt of phentolamine. Exemplary pharmaceutically acceptable salts include, for example, the hydrochloric acid salt and mesylate salt. Accordingly, in certain embodiments, the solution comprises phentolamine (i.e., as the free base). In certain other embodiments, the solution comprises phentolamine hydrochloride. In certain yet other embodiments, the solution comprises phentolamine mesylate.

The amount of phentolamine or a pharmaceutically acceptable salt thereof in the aqueous ophthalmic solution may be adjusted in order to achieve desired performance properties. For example, where is it desired to provide a larger amount of phentolamine (or pharmaceutically acceptable salt thereof) to the patient in a single administration of the aqueous ophthalmic solution, the concentration of phentolamine (or pharmaceutically acceptable salt thereof) is increased in the aqueous ophthalmic solution. Single administration of aqueous ophthalmic solutions having a higher concentration of phentolamine (or pharmaceutically acceptable salt thereof) may provide the patient with improved visual performance for a longer duration of time because more phentolamine (or pharmaceutically acceptable salt thereof) is administered to the patient.

Accordingly, in certain embodiments, the aqueous ophthalmic solution comprises from about 0.1% (w/v) to about 2% (w/v) of phentolamine or a pharmaceutically acceptable salt thereof. In certain embodiments, the aqueous ophthalmic solution comprises from about 0.25% (w/v) to about 2% (w/v) of phentolamine or a pharmaceutically acceptable salt thereof. In certain other embodiments, the aqueous ophthalmic solution comprises from about 0.5% (w/v) to about 2% (w/v) of phentolamine or a pharmaceutically acceptable salt thereof. In certain other embodiments, the aqueous ophthalmic solution comprises from about 0.25% (w/v) to about 1% (w/v) of phentolamine or a pharmaceutically acceptable salt thereof. In certain other embodiments, the aqueous ophthalmic solution comprises about 1% (w/v) of phentolamine or a pharmaceutically acceptable salt thereof. In certain other embodiments, the aqueous ophthalmic solution comprises from about 0.1% (w/v) to about 4% (w/v) of phentolamine mesylate. In certain other embodiments, the aqueous ophthalmic solution comprises from about 0.1% (w/v) to about 2% (w/v) of phentolamine mesylate. In certain other embodiments, the aqueous ophthalmic solution comprises from about 0.25% (w/v) to about 2% (w/v) of phentolamine mesylate. In certain other embodiments, the aqueous ophthalmic solution comprises from about 0.5% (w/v) to about 2% (w/v) of phentolamine mesylate. In certain other embodiments, the aqueous ophthalmic solution comprises from about 0.25% (w/v) to about 1% (w/v) of phentolamine mesylate. In certain other embodiments, the aqueous ophthalmic solution comprises about 1% (w/v) of phentolamine mesylate. In certain other embodiments, the aqueous ophthalmic solution comprises about 0.25% (w/v) or about 0.5% (w/v) of phentolamine mesylate.

Polyol Compounds

The aqueous ophthalmic solution comprises one or more polyol compounds. The polyol compound is an organic compound having at least two hydroxyl groups (e.g., from 2 to about 6 hydroxyl groups). The polyol compound is beneficial to the aqueous ophthalmic solution because, for example, it can increase the stability of the aqueous ophthalmic solution to storage and/or modify the tonicity of the aqueous ophthalmic solution. Exemplary polyol compounds include, for example, mannitol, glycerol, propylene glycol, ethylene glycol, sorbitol, and xylitol.

The aqueous ophthalmic solution may contain a single polyol compound or a mixture of one or more polyol compounds. In other words, the aqueous ophthalmic solution comprises at least one polyol compound. In certain embodiments, the aqueous ophthalmic solution comprises at least one polyol compound that is mannitol, glycerol, propylene glycol, ethylene glycol, sorbitol, or xylitol. In certain other embodiments, the at least one polyol compound is mannitol. In certain other embodiments, the at least one polyol compound is glycerol. In certain other embodiments, the at least one polyol compound is propylene glycol. In certain other embodiments, the at least one polyol compound is mannitol, and the solution further comprises glycerol. In certain other embodiments, the at least one polyol compound is mannitol, and the solution further comprises propylene glycol. In certain other embodiments, the at least one polyol compound is glycerol, and the solution further comprises propylene glycol. In certain other embodiments, the mannitol described in embodiments above is D-mannitol.

The amount of the at least one polyol compound in the aqueous ophthalmic solution may be selected in order to achieve desired performance properties for the solution. The polyol compound may, for example, increase the stability of the solution to storage and/or modify the tonicity of the solution to make it more suitable for administration to the eye of a patient. In certain embodiments, the aqueous ophthalmic solution comprises from about 2% (w/v) to about 5% (w/v) of the at least one polyol compound. In certain other embodiments, the aqueous ophthalmic solution comprises from about 3.5% (w/v) to about 4.5% (w/v) of the at least one polyol compound. In certain other embodiments, the aqueous ophthalmic solution comprises about 4% (w/v) of the at least one polyol compound. In certain other embodiments, the aqueous ophthalmic solution comprises from about 2% (w/v) to about 3% (w/v) mannitol, and about 0.5% (w/v) to about 1.5% (w/v) glycerin. In certain other embodiments, the mannitol described in embodiments above is D-mannitol.

In certain embodiments, the amount of polyol may be selected based on the amount of phentolamine (or pharmaceutically acceptable salt thereof), such that there is an inverse relationship between the amount of phentolamine (or pharmaceutically acceptable salt thereof) and the polyol in order to achieve isotonicity with the eye. For example, in embodiments where the aqueous ophthalmic solution contains about 2% (w/v) phentolamine, mannitol is present in the solution at a concentration of about 3% (w/v). In embodiments where the aqueous ophthalmic solution contains about 1% (w/v) phentolamine, mannitol is present in the solution at a concentration of about 4% (w/v). To further illustrate this principle, in embodiments where the aqueous ophthalmic solution contains about 0.5% (w/v) phentolamine, mannitol may be present in the solution at a concentration of about 4.5% (w/v). In certain embodiments, the mannitol described in embodiments above is D-mannitol.

It is appreciated that the aqueous ophthalmic solution can contain additional ingredients described herein, such as various polymer materials. One such embodiment is an aqueous ophthalmic solution comprising, for example, at least one polyol compound that is propylene glycol, and further comprising polypropylene glycol, such as polypropylene glycol having a weight average molecular weight in the range of about 5,000 g/mol to about 100,000 g/mol.

Poly($C_{2-4}$alkylene)glycol Polymer

The aqueous ophthalmic solution may optionally comprise a poly($C_{2-4}$alkylene)glycol polymer. An exemplary poly($C_{2-4}$alkylene)glycol polymer is polypropylene glycol, such as a polypropylene glycol having a weight average molecular weight in the range of about 5,000 g/mol to about 100,000 g/mol, about 10,000 g/mol to about 50,000 g/mol, or about 50,000 g/mol to about 100,000 g/mol.

Dextran

The aqueous ophthalmic solution may optionally comprise dextran. Dextran is a commercially available, branched polysaccharide comprising glucose molecules. The amount of dextran in the aqueous ophthalmic solution may be selected to achieve certain performance properties. In certain embodiments, the aqueous ophthalmic solution comprises from about 0.01% (w/v) to about 2% (w/v) dextran. In certain other embodiments, the aqueous ophthalmic solution comprises from about 0.01% (w/v) to about 1% (w/v) dextran.

The dextran may be further characterized according to its weight average molecular weight. In certain embodiments, the dextran has a weight average molecular weight in the range of about 65,000 g/mol to about 75,000 g/mol. In certain other embodiments, the dextran has a weight average molecular weight of about 70,000 g/mol. In yet other embodiments, the dextran has a weight average molecular weight in the range of about 5,000 g/mol to about 100,000 g/mol, about 10,000 g/mol to about 50,000 g/mol, or about 50,000 g/mol to about 100,000 g/mol.

Cellulose Agent

The aqueous ophthalmic solution may optionally comprise a cellulose agent. Exemplary cellulose agents include, for example, cellulose, carboxymethyl cellulose, hydroxyethylcellulose, hydroxypropylcellulose, and hydroxypropylmethyl cellulose. In certain embodiments, the cellulose agent is hydroxypropylmethyl cellulose. In certain other embodiments, the cellulose agent is cellulose, carboxymethyl cellulose, hydroxyethylcellulose, or hydroxpropylcellulose. The amount of cellulose agent in the aqueous ophthalmic solution may be selected in order to achieve desired performance properties. For example, in certain embodiments, the aqueous ophthalmic solution comprises from about 0.01% (w/v) to about 2% (w/v) cellulose agent.

The cellulose agent may be further characterized according to its weight average molecular weight. In certain embodiments, the cellulose agent has a weight average molecular weight in the range of about 5,000 g/mol to about 100,000 g/mol, about 10,000 g/mol to about 50,000 g/mol, or about 50,000 g/mol to about 100,000 g/mol.

Buffer

The aqueous ophthalmic solution comprises at least one buffer. The buffer imparts to the solution a buffering capacity, that is, the capacity to neutralize, within limits, either acids or bases (alkali) with relatively little or no change in the original pH. The buffer may be an acid, a base, or a combination of an acid and a base. The buffer may be organic, inorganic, or a combination of organic and inorganic components. It should be understood that the buffer at least partially dissociates in aqueous solution to form a mixture of, e.g., an acid and conjugate base or a base and conjugate acid. For example, the buffer may be a combination of a carboxylic acid and its carboxylate salt. In another embodiment, the buffer may be a combination of an acid and a base, where the acid and the base are not conjugates. For example, the acid may be boric acid and the base may be tris(hydroxymethyl)aminomethane (TRIS).

Exemplary buffers include organic acids (e.g., acetic acid, sorbic acid, and oxalic acid), a borate salt, a hydrogen carbonate salt, a carbonate salt, a gluconate salt, a lactate salt, a phosphate salt, a propionate salt, a perborate salt, tris-(hydroxymethyl)aminomethane (TRIS), bis(2-hydroxyethyl)-imino-tris-(hydroxymethyl)aminoalcohol (bis-tris), N-[2-hydroxy-1,1-bis(hydroxymethyl)ethyl]glycine (tricene), N-[2-hydroxy-1,1-bis(hydroxymethyl)ethyl]glycine, 3-(N-morpholino)propanesulfonic acid, N-(carbamoylmethyl)taurine (ACES), an amino acid, salts thereof, and combinations thereof. It should be understood that the salt form of a buffer may comprise any suitable counterion. For example, the salt form of an acid may comprise an alkali or alkaline earth metal counterion.

The buffer can be characterized according to its strength, i.e., the buffering capacity. The buffering capacity can be tested, for example, by determining the millimoles (mM) of strong acid or base (or respectively, hydrogen or hydroxide ions) required to change the pH of a buffer solution by one unit when added to one liter (a standard unit) of the buffer solution. The buffering capacity generally depends on the type and concentration of the buffer components and can be greater in particular pH ranges. For example, a buffer may have an optimal buffering capacity in a pH range near the $pK_a$ of the buffer, e.g., within about 1 pH unit or within about 2 pH units of the $pK_a$ the buffer. In certain embodiments, the buffer is a weak buffer, such as an alkali metal carboxylate (e.g., sodium acetate).

In certain embodiments, the buffer is a weak acid buffer having one or more of the following characteristics: (a) a pKa of from about 4.0 to about 6.0; more preferably, from about 4.5 to about 5.5; and (b) a lipophilicity value Log P of from about −0.50 to about 1.5; more preferably, from about −0.25 to about 1.35.

The amount of buffer can be adjusted in order to achieve desired performance properties for the aqueous ophthalmic solution. For example, in certain embodiments, the buffer may be present at a concentration of less than about 10 mM, less than about 7 mM, less than about 5 mM, less than about 3 mM, or less than about 2 mM. In some embodiments, the buffer may be present at a concentration of from about 1 mM to about 10 mM, from about 1 mM to about 7 mM, from about 1 mM to about 5 mM, from about 1 mM to about 3 mM, from about 1 mM to about 2 mM, from about 2 mM to about 5 mM, or from about 2 mM to about 3 mM. In yet other embodiments, the buffer is present at a concentration of about 3 mM.

The amount and identity of the buffer may be selected in order to achieve certain performance properties for the aqueous ophthalmic solution. For example, the amount of buffer may impact the quantity of acid that may be neutralized before there is substantial change in the pH of the aqueous ophthalmic solution. Also, the amount of buffer may impact the tonicity of the aqueous ophthalmic solution. Desirably, the quantity and identity of the buffer should be selected in order to minimize any irritation that may be caused by administration of the aqueous ophthalmic solution to the eye of a patient. Accordingly, in certain embodiments, the buffer is present at a concentration in the range of about 2 mM to about 4 mM. In yet other embodiments, the buffer is present at a concentration of about 3 mM. In certain embodiments, the buffer comprises an alkali metal alkylcarboxylate. In certain other embodiments, the buffer comprises an alkali metal acetate. In yet other embodiments, the buffer comprises sodium acetate.

Solution pH

The aqueous ophthalmic solution may be characterized according to the pH of the solution. Desirably, the aqueous ophthalmic solution has a pH in the range of 4.0 to 7.5. In certain embodiments, the aqueous ophthalmic solution has a pH in the range of 4.5 to 7.5. In certain embodiments, the solution has a pH in the range of 4.5 to 6.0. In certain other embodiments, the solution has a pH in the range of 4.5 to 5.5. In yet other embodiments, the solution has a pH in the range of 4.7 to 5.1.

Additional Materials for Aqueous Ophthalmic Solutions

The aqueous ophthalmic solutions may contain additional materials in order to make the composition more suitable for administration to the eye of a patient. Exemplary additional materials are described below and include, for example, a tonicity modifier, preservative, antioxidant, viscosity modifying agent, stabilizing agent, corneal permeation enhancing agent, and surfactants.

A. Tonicity Modifier

The aqueous ophthalmic solution may optionally comprise one or more tonicity modifiers. The tonicity modifier may be ionic or non-ionic. In certain embodiments, the tonicity modifier may be a salt, a carbohydrate, or a polyol. Exemplary tonicity modifiers include alkali metal or alkaline earth metal halides (such as LiBr, LiCl, LiI, KBr, KCl, KI, NaBr, NaCl, NaI, $CaCl_2$, and $MgCl_2$), boric acid, dextran (e.g., Dextran 70), cyclodextrin, dextrose, mannitol, glycerin, urea, sorbitol, propylene glycol, or a combination thereof.

It is appreciated that the tonicity modifier may be added to the aqueous ophthalmic solution in an amount sufficient to provide a desired osmolality. In certain embodiments, the tonicity modifier is present in the aqueous ophthalmic solution in an amount sufficient so that the aqueous ophthalmic solution has an osmolality ranging from about 50 to about 1000 mOsm/kg, from about 100 to about 400 mOsm/kg, from about 200 to about 400 mOsm/kg, or from about 280 to about 380 mOsm/kg. In certain embodiments, a tonicity modifier may be present in an amount ranging from about 0.01% (w/v) to about 7% (w/v), about 0.01% (w/v) to about 5% (w/v), about 0.01% (w/v) to about 1% (w/v), about 0.1% (w/v) to about 1% (w/v), about 0.05% (w/v) to about 5% (w/v), about 0.05% (w/v) to about 0.5% (w/v), about 1% (w/v) to about 3% (w/v), or about 2% (w/v) to about 4% (w/v), of the aqueous ophthalmic solution.

B. Preservative

The aqueous ophthalmic solution may optionally comprise one or more preservatives in order to, for example, reduce or prevent microbial contamination. Exemplary preservatives include quaternary ammonium salts such as polyquaternium-1, cetrimide, benzalkonium chloride, or benzoxonium chloride; alkyl-mercury salts of thiosalicylic acid such as thiomersal, phenylmercuric nitrate, phenylmercuric acetate, or phenylmercuric borate; parabens such as methylparaben or propylparaben; alcohols such as chlorobutanol, benzyl alcohol, phenyl ethanol, cyclohexanol, 3-pentanol, or resorcinol; a peroxide; chlorine dioxide or PURITE; guanidine derivatives such as chlorohexidine gluconate or polyaminopropyl biguanide; and combinations thereof.

The amount of preservative can be adjusted in order to achieve desired performance properties for the aqueous ophthalmic solution. In certain embodiments, the preservative is present in an amount less than about 5% (w/v), 3% (w/v), 1% (w/v), or 0.1% (w/v) of the aqueous ophthalmic solution. In certain other embodiments, the preservative is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

C. Antioxidant

The aqueous ophthalmic solution may optionally comprise one or more antioxidants. Exemplary antioxidants for use in the aqueous ophthalmic solutions described herein include water soluble antioxidants such as ascorbic acid, cysteine hydrochloride, sodium bisulfate, sodium metabisulfite, sodium bisulfite, sodium sulfite, and the like; and oil-soluble antioxidants, such as ascorbyl palmitate, butylated hydroxyanisole (BHA), butylated hydroxytoluene (BHT), lecithin, propyl gallate, alpha-tocopherol, and the like.

The amount of antioxidant can be adjusted in order to achieve desired performance properties for the aqueous ophthalmic solution. In certain embodiments, the antioxidant is present in an amount less than about 5% (w/v), 3% (w/v), 1% (w/v), or 0.1% (w/v) of the aqueous ophthalmic solution. In certain other embodiments, the antioxidant is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

D. Viscosity Modifying Agent

The aqueous ophthalmic solution may optionally comprise one or more viscosity modifying agents. The viscosity modifying agent may be used, for example, to increase the absorption of an active agent or increase the retention time of the aqueous ophthalmic solution in the eye. Exemplary viscosity modifying agents include polyvinylpyrrolidone, methylcellulose, hydroxypropyl methylcellulose, hydroxyethylcellulose, hydroxpropylcellulose, carboxymethylcellulose (CMC) and salts thereof (e.g., CMC sodium salt), gelatin, cellulose glycolate, sorbitol, niacinamide, an alpha-cyclodextran, polyvinyl alcohol, polyethylene glycol, hyaluronic acid, a polysaccharide, a monosaccharide, and combinations thereof.

The amount of viscosity modifying agent can be adjusted in order to achieve desired performance properties for the aqueous ophthalmic solution. In certain embodiments, the viscosity modifying agent is present in an amount less than about 10% (w/v), 5% (w/v), 3% (w/v), 1% (w/v), or 0.1% (w/v) of the aqueous ophthalmic solution. In certain other embodiments, the viscosity modifying agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution. In certain other embodiments, the viscosity modifying agent is present in an amount sufficient to provide an aqueous ophthalmic solution with a viscosity in the range of about 30 centipoise to about 100 centipoise.

E. Corneal Permeation Enhancing Agent

The aqueous ophthalmic solution may optionally comprise one or more agents for enhancing corneal permeation of phentolamine (or a pharmaceutically acceptable salt thereof). Exemplary agents for enhancing corneal permeation include polymers, organic acids, esters of an organic acid (e.g., a monoglyceride of fatty acid having 8 to 12 carbon atoms), cyclodextrin, benzalkonium chloride (BAK), EDTA, caprylic acid, citric acid, boric acid, sorbic acid, polyoxyethylene-20-stearyl ether (PSE), polyethoxylated castor oil (PCO), deoxycholic acid sodium salt (DC), cetylpyridinium chloride (CPC), laurocapram, hexamethylenelauramide, hexamethyleneoctanamide, decylmethylsulfoxide, methyl sulfone, dimethyl sulfoxide, and combinations thereof.

The amount of corneal permeation enhancing agent can be adjusted in order to achieve desired performance properties for the aqueous ophthalmic solution. In certain embodiments, the corneal permeation enhancing agent is present in an amount less than about 10% (w/v), 5% (w/v), 1% (w/v), or 0.1% (w/v) of the aqueous ophthalmic solution. In certain other embodiments, the corneal permeation enhancing agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), about 0.05% (w/v) to about 0.5% (w/v), about 1% (w/v) to about 3% (w/v), or about 2% (w/v) to about 4% (w/v), of the aqueous ophthalmic solution.

F. Solubilizing Agent

The aqueous ophthalmic solution may optionally comprise one or more solubilizing agents to improve the solubility of phentolamine (or a pharmaceutically acceptable salt thereof) in the aqueous ophthalmic solution. Exemplary solubilizing agents include, for example, a fatty acid glycerol poly-lower alkylene (i.e., a $C_1$ to $C_7$, linear or branched) glycol ester, fatty acid poly-lower alkylene glycol ester, polyalkylene glycol (e.g., polyethylene glycol), glycerol ether of vitamin E, tocopherol polyethylene glycol 1000 succinate (TPGS), tyloxapol, polysorbate 20, polysorbate 40, polysorbate 60, polysorbate 80, polyoxyethylene/polyoxypropylene surfactants (e.g., Pluronic F-68, F-84 and P-103), cyclodextrin, and combinations thereof.

The amount of solubilizing agent can be adjusted in order to achieve desired performance properties for the aqueous ophthalmic solution. In certain embodiments, the solubilizing agent is present in an amount less than about 10% (w/v), 5% (w/v), 3% (w/v), 1% (w/v), or 0.1% (w/v) of the aqueous ophthalmic solution. In certain other embodiments, the solubilizing agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

G. Stabilizing Agent

The aqueous ophthalmic solution may optionally comprise one or more stabilizing agents in order to improve the stability of the aqueous ophthalmic solution to storage, etc. Stabilizing agents described in the pharmaceutical literature are contemplated to be amenable for use in the aqueous ophthalmic solutions described herein. Exemplary stabilizing agents include an alcohol (e.g., polyols, such as mannitol, glycerol, propylene glycol, sorbitol, and xylitol), polyalkylene glycols such as polyethylene glycol, polypropylene glycol, polyethylene glycol-nonphenol ether, polyethylene glycol sorbitan monolaurate, polyethylene glycol sorbitan monooleate, polyethylene glycol sterarate, polyethylene glycol polypropylene glycol ether, polyvinyl alcohol, polyvinyl pyrrolidine, ascorbic acid, vitamin E, N-acetylcarnosine (NAC), sorbic acid, and combinations thereof. In certain embodiments, the stabilizing agent is a polymer, such as one of the polymers mentioned above.

The amount of stabilizing agent can be adjusted in order to achieve desired performance properties for the aqueous ophthalmic solution. In certain embodiments, the stabilizing agent is present in an amount less than about 10% (w/v), 5% (w/v), or 1% (w/v) of the aqueous ophthalmic solution. In certain other embodiments, the stabilizing agent is present in an amount ranging from about 0.01% (w/v) to about 5% (w/v), about 0.01% (w/v) to about 1% (w/v), or about 0.01% (w/v) to about 0.1% (w/v) of the aqueous ophthalmic solution.

H. Surfactant

The aqueous ophthalmic solution may optionally comprise one or more surfactants. Exemplary surfactants include Polysorbate 20 (i.e., polyoxyethylene (20) sorbitan monolaurate), Polysorbate 40 (i.e., polyoxyethylene (20) sorbitan monopalmitate), Polysorbate 60 (i.e., polyoxyethylene (20) sorbitan monostearate), Polysorbate 80 (i.e., polyoxyethylene (20) sorbitan monooleate), glyceryl stearate, isopropyl stearate, polyoxyl stearate, propylene glycol stearate, sucrose stearate, polyethylene glycol, a polypropylene oxide, a polypropylene oxide copolymer, Pluronic F68, Pluronic F-84, Pluronic P-103, an alcohol ethoxylate, an alkylphenol ethoxylate, an alkyl glycoside, an alkyl polyglycoside, a fatty alcohol, hydroxypropylmethyl cellulose (HPMC), carboxymethyl cellulose (CMC), cyclodextrin, a polyacrylic acid, phosphatidyl chloline, phosphatidyl serine, and combinations thereof.

The amount of surfactant can be adjusted in order to achieve desired performance properties for the aqueous ophthalmic solution. In certain embodiments, the surfactant is present in an amount less than about 10% (w/v), 5% (w/v), 3% (w/v), 1% (w/v), or 0.1% (w/v) of the aqueous ophthalmic solution. In certain other embodiments, the surfactant is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

I. Demulcent Polymers

The aqueous ophthalmic solution may optionally comprise one or more demulcent polymers. Because of their ability to hold large amounts of water, demulcent polymers are useful for coating and moisturizing the cornea of the eye. Exemplary demulcent polymers include cellulose derivatives, dextran 40, dextran 70, gelatin, and liquid polyols.

J. Wetting Agents

The aqueous ophthalmic solution may optionally comprise one or more wetting agents. Wetting agents can be used to wet the surface of the eye. Exemplary wetting agents include polysorbates, poloxamers, tyloxapol, and lecithin.

K. Additional Materials

The aqueous ophthalmic solutions may optionally comprise one or more additional materials, such as acetylcysteine, cysteine, sodium hydrogen sulfite, butyl-hydroxyanisole, butyl-hydroxytoluene, alpha-tocopherol acetate, thiourea, thiosorbitol, sodium dioctyl sulfosuccinate, monothioglycerol, lauric acid sorbitol ester, triethanol amine oleate, or palmitic acid esters.

Further, the aqueous ophthalmic solutions may comprise a carrier, such as one or more of the exemplary carriers are described in for example, Martin, Remington's Pharmaceutical Sciences, 15th Ed., Mack Publ. Co., Easton, Pa. [1975]). The carrier can be, for example, a mixture of water and a water-miscible solvent (e.g., an alcohol such as glycerin, a vegetable oil, or a mineral oil). Other exemplary carriers include a mixture of water and one or more of the following materials: hydroxyethylcellulose, carboxymethylcellulose, methylcellulose, an alkali metal salt of carboxymethylcellulose, hydroxymethylcellulose, methylhydroxypropylcellulose, hydroxypropylcellulose, ethyl oleate, polyvinylpyrrolidone, an acrylate polymer, a methacrylate polymer, a polyacrylamide, gelatin, an alginate, a pectin, tragacanth, karaya gum, xanthan gum, carrageenin, agar, acacia, a starch (such as starch acetate or hydroxypropyl starch), polyvinyl alcohol, polyvinyl methyl ether, polyethylene oxide, or a cross-linked polyacrylic acid.

Exemplary Aqueous Ophthalmic Solutions

The aqueous ophthalmic solutions having been generally described above will now be more specifically described by reference to the following more specific examples. The following more specific examples are only exemplary and are not intended to limit the scope of the invention in any way.

One such exemplary solution is an aqueous ophthalmic solution free of a chelating agent comprising: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.25% (w/v) to about 1% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4 to 6.

Another such exemplary solution is an aqueous ophthalmic solution free of a chelating agent comprising: (a) about 0.5% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about 2% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Another such exemplary solution is an aqueous ophthalmic solution free of a chelating agent comprising: (a) about 0.25% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain other embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about 1% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Further exemplary aqueous ophthalmic solutions are provided in Tables 1-3 below, where in each instance the solution has a pH in the range of 4.7 to 5.1.

TABLE 1

EXEMPLARY AQUEOUS OPHTHALMIC SOLUTIONS.

| Component | Formulation No. | | | | | | | |
|---|---|---|---|---|---|---|---|---|
| | A1 | B1 | C1 | D1 | E1 | F1 | G1 | H1 |
| Phentolamine mesylate (% w/v) | 1.5 | 1 | 0.5 | 1 | 1 | 1 | 1 | 1 |
| Mannitol (% w/v) | 4 | 4 | 4 | 3 | 3 | 2 | 2 | 4 |
| Sodium acetate (mM) | 3 | 3 | 3 | 3 | 3 | 3 | 3 | 3 |
| Glycerol (% w/v) | 0 | 0 | 0 | 0.5 | 0 | 1 | 0 | 0 |
| Propylene glycol (% w/v) | 0 | 0 | 0 | 0 | 0.5 | 0 | 1 | 0 |
| Dextran 70 (% w/v) | 0 | 0 | 0 | 0 | 0 | 0 | 0 | 0.1 |
| Water | q.s. | q.s. | q.s. | q.s. | q.s. | q.s. | q.s. | q.s. |

TABLE 2

EXEMPLARY AQUEOUS OPHTHALMIC SOLUTIONS.

| Component | Formulation No. | | | | | |
|---|---|---|---|---|---|---|
| | A2 | B2 | C2 | D2 | E2 | F2 |
| Phentolamine mesylate (% w/v) | 0.25 | 0.25 | 0.25 | 0.25 | 0.25 | 0.25 |
| Mannitol (% w/v) | 4 | 3 | 3 | 2 | 2 | 4 |
| Sodium acetate (mM) | 3 | 3 | 3 | 3 | 3 | 3 |
| Glycerol (% w/v) | 0 | 0.5 | 0 | 1 | 0 | 0 |
| Propylene glycol (% w/v) | 0 | 0 | 0.5 | 0 | 1 | 0 |
| Dextran 70 (% w/v) | 0 | 0 | 0 | 0 | 0 | 0.1 |
| Water | q.s. | q.s. | q.s. | q.s. | q.s. | q.s. |

TABLE 3

EXEMPLARY AQUEOUS OPHTHALMIC SOLUTIONS.

| Component | Formulation No. | | | | | | | |
|---|---|---|---|---|---|---|---|---|
| | A3 | B3 | C3 | D3 | E3 | F3 | G3 | H3 |
| Phentolamine mesylate (% w/v) | 1.5 | 1 | 0.5 | 0.25 | 1 | 1 | 1 | 1 |
| Mannitol (% w/v) | 4 | 4 | 4 | 4 | 3 | 2 | 2 | 4 |
| Sodium acetate (mM) | 3 | 3 | 3 | 3 | 3 | 3 | 2 | 3 |
| Water | q.s. | q.s. | q.s. | q.s. | q.s. | q.s. | q.s. | q.s. |

Another exemplary aqueous ophthalmic solution comprises phentolamine mesylate (e.g., at 1% w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 1% w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of 4 to 6. In certain other embodiments, the aqueous ophthalmic solution consists of phentolamine mesylate (e.g., at 1% w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of 4.5 to 5.1.

Another exemplary aqueous ophthalmic solution comprises phentolamine mesylate (e.g., at 1% w/v), mannitol (e.g., at 4% w/v), sodium acetate (e.g., at 3 mM), and water, wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 1% w/v), mannitol (e.g., at 4% w/v), sodium acetate (e.g., at 3 mM), and water, wherein the solution has a pH in the range of 4 to 6. In certain embodiments, the aqueous ophthalmic solution comprises phentolamine mesylate at 1% w/v, mannitol 4% w/v, sodium acetate at 3 mM, and water, wherein the solution has a pH in the range of 4.5 to 5.1. In certain other embodiments, the aqueous ophthalmic solution consists of phentolamine mesylate (e.g., at 1% w/v), mannitol (e.g., at 4% w/v), sodium acetate (e.g., at 3 mM), and water, wherein the solution has a pH in the range of 4.5 to 5.1. In certain embodiments, the aqueous ophthalmic solution consists essentially of phentolamine mesylate at 1% w/v, mannitol 4% w/v, sodium acetate at 3 mM, and water, wherein the solution has a pH in the range of 4.5 to 5.1.

Yet another exemplary solution is an aqueous ophthalmic solution free of a chelating agent that comprises: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

Yet another exemplary solution is an aqueous ophthalmic solution free of a chelating agent that comprises: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.1% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.5 to 5.2 and does not contain a chelating agent.

Yet another exemplary solution is an aqueous ophthalmic solution free of a chelating agent that comprises: (a) about 0.5% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.5% (w/v) to about 1% (w/v) of phentolamine mesylate; (b) about 3% (w/v) to about 5% (w/v) of mannitol; (c) about 1 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.1% (w/v) to about 1% (w/v) of phentolamine mesylate; (b) about 4% mannitol; (c) about 3 mM sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.5% (w/v) to about 1% (w/v) of phentolamine mesylate; (b) about 4% mannitol; (c) about 3 mM sodium acetate; and (d) water; wherein the solution has a pH in the range of 4.6 to 5.2 and does not contain a chelating agent.

Stability Features of Aqueous Ophthalmic Solutions

The aqueous ophthalmic solutions described herein may be further characterized according to their stability features, such as the percentage of phentolamine (or pharmaceutically acceptable salt thereof) that is present in the aqueous ophthalmic solution after storage for a certain length of time. As explained above, one of the benefits of the present aqueous ophthalmic solutions is that they possess good stability over extended periods of time, even though they do not have a chelating agent.

Accordingly, in certain embodiments, the aqueous ophthalmic solution is characterized by less than 2% by weight of the phentolamine or pharmaceutically acceptable salt thereof degrades upon storage of the solution at 25° C. for 12 weeks. In certain other embodiments, the aqueous ophthalmic solution is characterized by less than 2% by weight of the phentolamine or pharmaceutically acceptable salt thereof degrades upon storage at 25° C. for 24 weeks (or 36 weeks or 48 weeks). In yet other embodiments, less than 7% by weight of the phentolamine or pharmaceutically acceptable salt thereof degrades upon storage at 40° C. for 12 weeks (or 24, 36, or 48 weeks). In yet other embodiments, the aqueous ophthalmic solution is characterized by less than 10% by weight of the phentolamine or pharmaceutically acceptable salt thereof degrades upon storage at 25° C. for 18 months, 24 months, or 36 months. In yet other embodiments, the aqueous ophthalmic solution is characterized by less than 10% by weight of the phentolamine or pharmaceutically acceptable salt thereof degrades upon storage at temperature in the range of 2-8° C. for 18 months, 24 months, or 36 months. In yet other embodiments, the aqueous ophthalmic solution is characterized by less than 4% by weight (or preferably less than 3% by weight) of the phentolamine or pharmaceutically acceptable salt thereof degrades upon storage at 25° C. for 18 months, 24 months, or 36 months. In yet other embodiments, less than 10% by weight of the phentolamine or pharmaceutically acceptable salt thereof degrades upon storage at 40° C. for 4, 5, or 6 months.

Polyvinylpyrrolidone Artificial Tears Formulation

Another ophthalmic solution contemplated for use in the present invention includes, polyvinylpyrrolidone artificial tears formulations, such as those described in, for example, U.S. Pat. Nos. 5,895,654; 5,627,611; and 5,591,426; and U.S. Patent Application Publication No. 2002/0082288, all of which are hereby incorporated by reference. Artificial tears formulations are understood to promote wettability and spread, have good retention and stability on the eye, and desirably do not cause any significant discomfort to the user. Accordingly, an exemplary polyvinylpyrrolidone artificial tear composition comprises: (1) polyvinylpyrrolidone, preferably in the amount of about 0.1-5% by weight of the solution; (2) benzalkonium chloride, preferably in an amount of about 0.01-0.10% by weight of the solution; (3) hydroxypropyl methylcellulose, preferably in an amount of about 0.2-1.5% by weight of the solution; (4) glycerin, preferably in an amount of about 0.2-1.0% by weight of the solution, and (5) water, wherein the pharmaceutical composition is an aqueous solution having isotonic properties.

III. Medical Kits

Another aspect of the invention provides a medical kit comprising, for example, (i) an ophthalmic solution described herein, and (ii) instructions for administering the ophthalmic solution according to methods described herein.

EXAMPLES

The invention now being generally described, will be more readily understood by reference to the following examples, which are included merely for purposes of illustrating certain aspects and embodiments of the present invention, and are not intended to limit the invention.

Example 1

A clinical study was performed in which phentolamine mesylate was administered to eyes of patients suffering from severe night vision difficulty. Experimental procedures and results are described below.

Part I—Experimental Procedures

Sixty patients with normal day vision (i.e., 20/40 or better) but which suffer from severe night vision difficulty were enrolled in the study. During the first period of the study, patients were randomized into three groups. The groups received either placebo, 0.5% (w/v) phentolamine mesylate, or 1.0% (w/v) phentolamine mesylate once daily for 15 days. The patients were observed on days 1, 4, 8, and 15 prior to administering the ophthalmic solution of phentolamine mesylate and then observed again two hours after the ophthalmic solution of phentolamine mesylate was administered. During the second period of the study, all sixty patients were instructed to administer an ophthalmic solution of phentolamine mesylate (1% (w/v)) as needed, but no more than once daily to each eye. The ophthalmic solution of phentolamine mesylate contained: 1% (w/v) phentolamine mesylate, 4% (w/v) mannitol, 3 mM sodium acetate, and water. The placebo was a solution containing 4% (w/v) mannitol, 3 mM sodium acetate, and water.

Patients in the study satisfied the following criteria: (1) 18-45 years of age and suffer from severe night vision difficulty, (2) 0.3 log improvement at two of five spatial frequencies (1.5, 3, 6, 12, and 18 cycles per degree) in at least one eye before and during illumination of the contralateral eye, using the Holladay Automated Contrast Sensitivity System test under mesopic room illumination with glare, and (3) photopic distance high-contrast visual acuity (corrected or uncorrected) of 20/40 or better in at least one eye.

Patients were to meet with a clinician for evaluation on study days 1, 4, 8, 15, and a post-dosing follow-up evaluation three or more days after administering the last dose in the second period. When patients met with the clinician, the following observations were made by the clinician: (1) mesopic contrast sensitivity with and without glare using the Holladay Automated Contrast Sensitivity System test, (2) mesopic distance high-contrast visual acuity using E-ET- DRS Acuity Testing, (3) mesopic distance low-contrast visual acuity using E-ETDRS Acuity Testing, (4) photopic distance high-contrast visual acuity using E-ETDRS Acuity Testing, and (5) eye redness using the Cornea and Contact Lens Research Unit (CCLRU) Redness Grading Scale developed by the School of Optometry, University of New South Wales, but that the grading scale was as follows: (0) none, (0.5) very slight, (1) slight, (2) moderate, and (3) severe.

The primary efficacy endpoint is an increase of at least 0.3 log (50% or more improvement) in mesopic contrast sensitivity with glare at two or more frequencies at 1.5, 3, 6, 12, and 18 cycles per degree, measured with Holladay Automated Contrast Sensitivity System methodology.

Part II—Results

Figure 2:
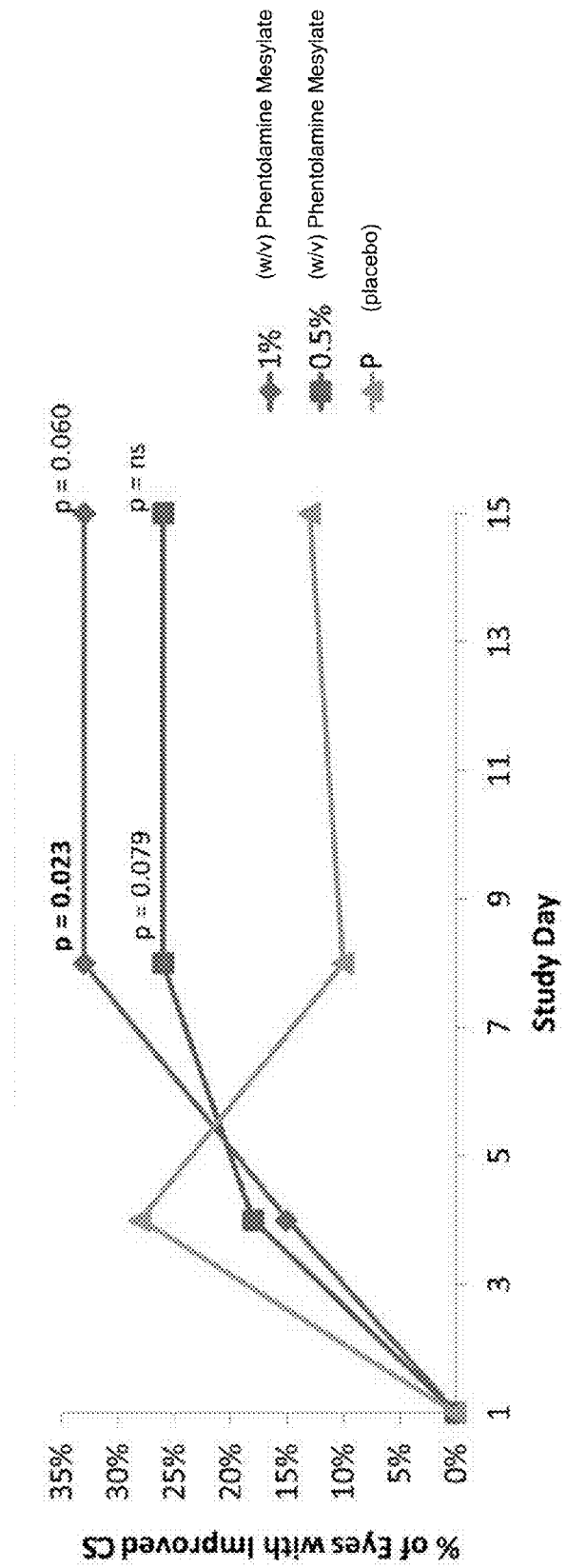
FIG. 2 is a line graph showing the percentage of eyes that showed at least a 50% improvement in contrast sensitivity relative to baseline prior to daily administration of phentolamine mesylate, as described in Example 1 where the patient's contrast sensitivity was measured on days 1, 4, 8, and 15 of the study prior to administration of that day's dose.

Results from the study are depicted in FIGS. 1-10. FIG. 1 shows that, beginning with day 8 of the study, greater than 20% of eyes tested after daily administration of phentolamine mesylate showed at least a 50% improvement in the contrast sensitivity measurement relative to baseline. FIG. 2 shows that, beginning with day 8 of the study, greater than 20% of eyes tested prior to administration of phentolamine mesylate on that day showed at least a 50% improvement in the contrast sensitivity measurement relative to baseline. Further, the data in FIGS. 1 and 2 show that no diminution in efficacy was observed with repeated dosing of phentolamine mesylate during the 15-day study period.

Figure 3:
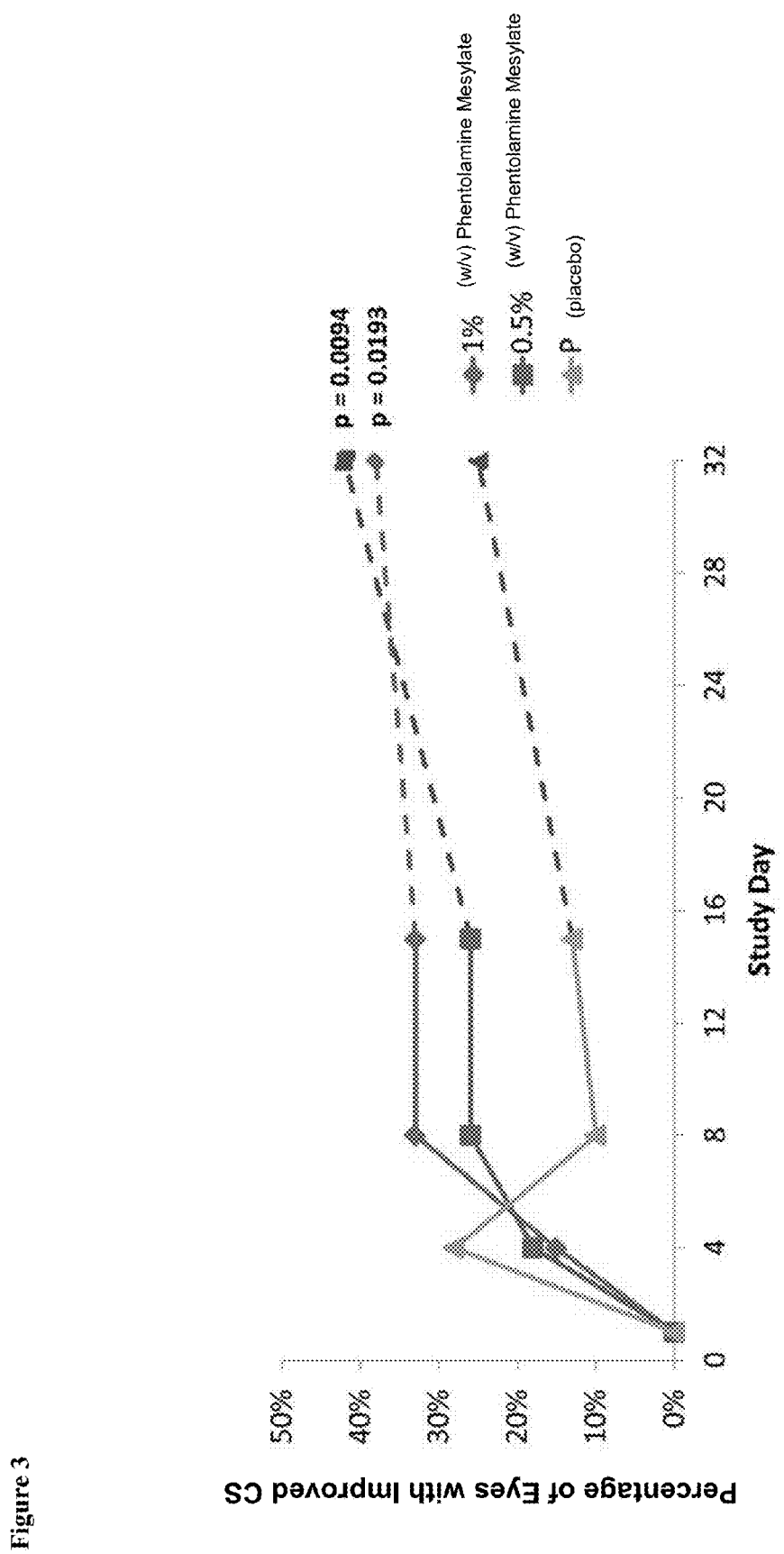
FIG. 3 is a line graph showing the percentage of eyes that showed at least a 50% improvement in contrast sensitivity relative to baseline prior to daily administration of phentolamine mesylate, as described in Example 1 where the patient's contrast sensitivity was measured on days 1, 4, 8, 15, and 32 of the study prior to administration of that day's dose.
Figure 4A:
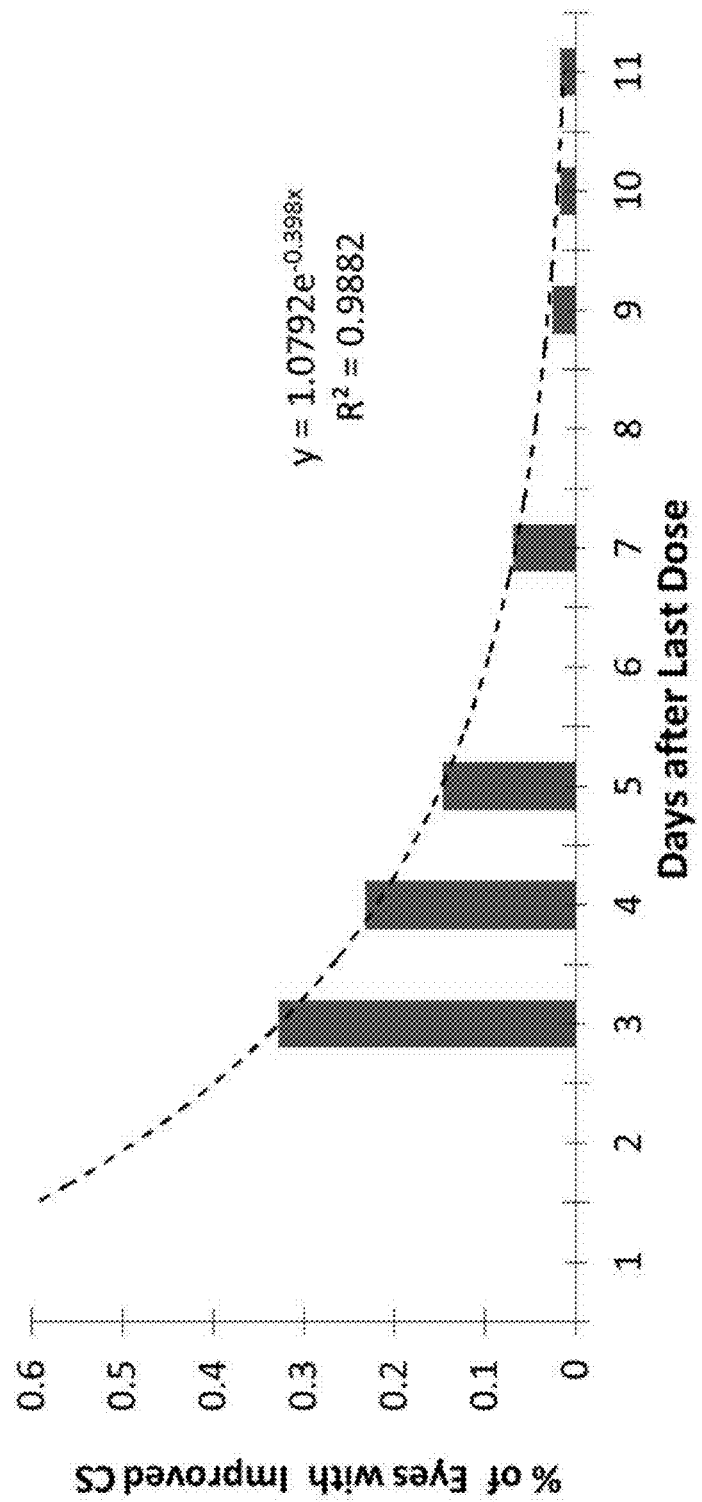
FIG. 4A is a bar graph showing the percentage of eyes with at least a 50% improvement in contrast sensitivity after the last dose of phentolamine mesylate during the second period of the study, as described in Example 1.
Figure 4B:
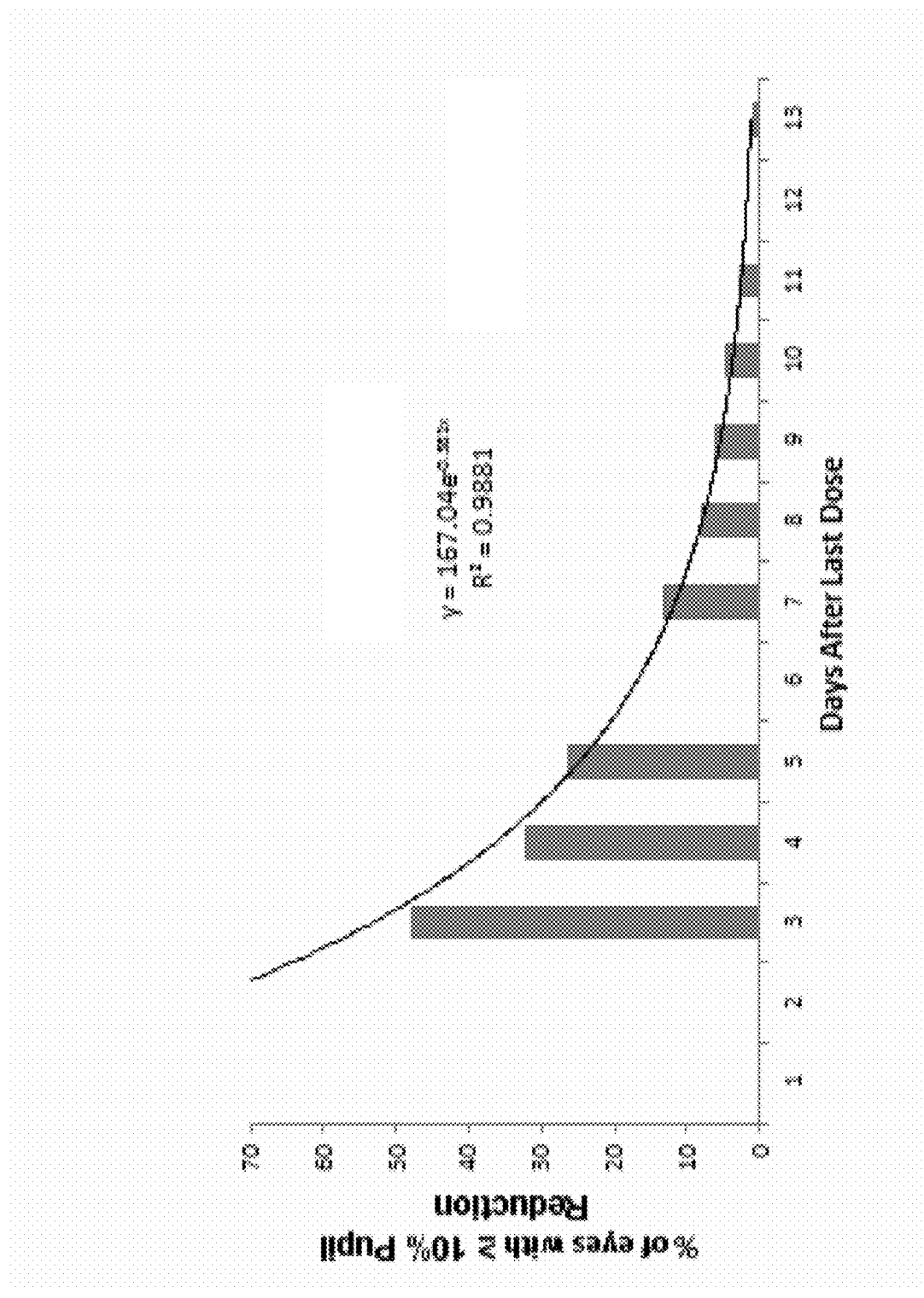
FIG. 4B is a bar graph showing the percentage of eyes with at least a 10% reduction in pupil diameter after the last dose of phentolamine mesylate during the second period of the study, as described in Example 1.

FIG. 3 shows that the percentage of eyes with at least a 50% improvement contrast sensitivity measured prior to that day's administration of phentolamine mesylate increased from day 15 to day 32 of the study. FIG. 4A is a bar graph showing the percentage of eyes with at least a 50% improvement in contrast sensitivity after the last dose of phentolamine mesylate during the second period of the study. Data in FIG. 4A demonstrates that the dosing protocol using phentolamine mesylate resulted in a pharmacokinetic half-life of approximately two days. FIG. 4B is a bar graph showing the percentage of eyes with at least a 10% reduction in pupil diameter after the last dose of phentolamine mesylate during the second period of the study. Data in FIG. 4B further demonstrates that the dosing protocol using phentolamine mesylate resulted in a pharmacokinetic half-life of approximately two days.

Figure 5:
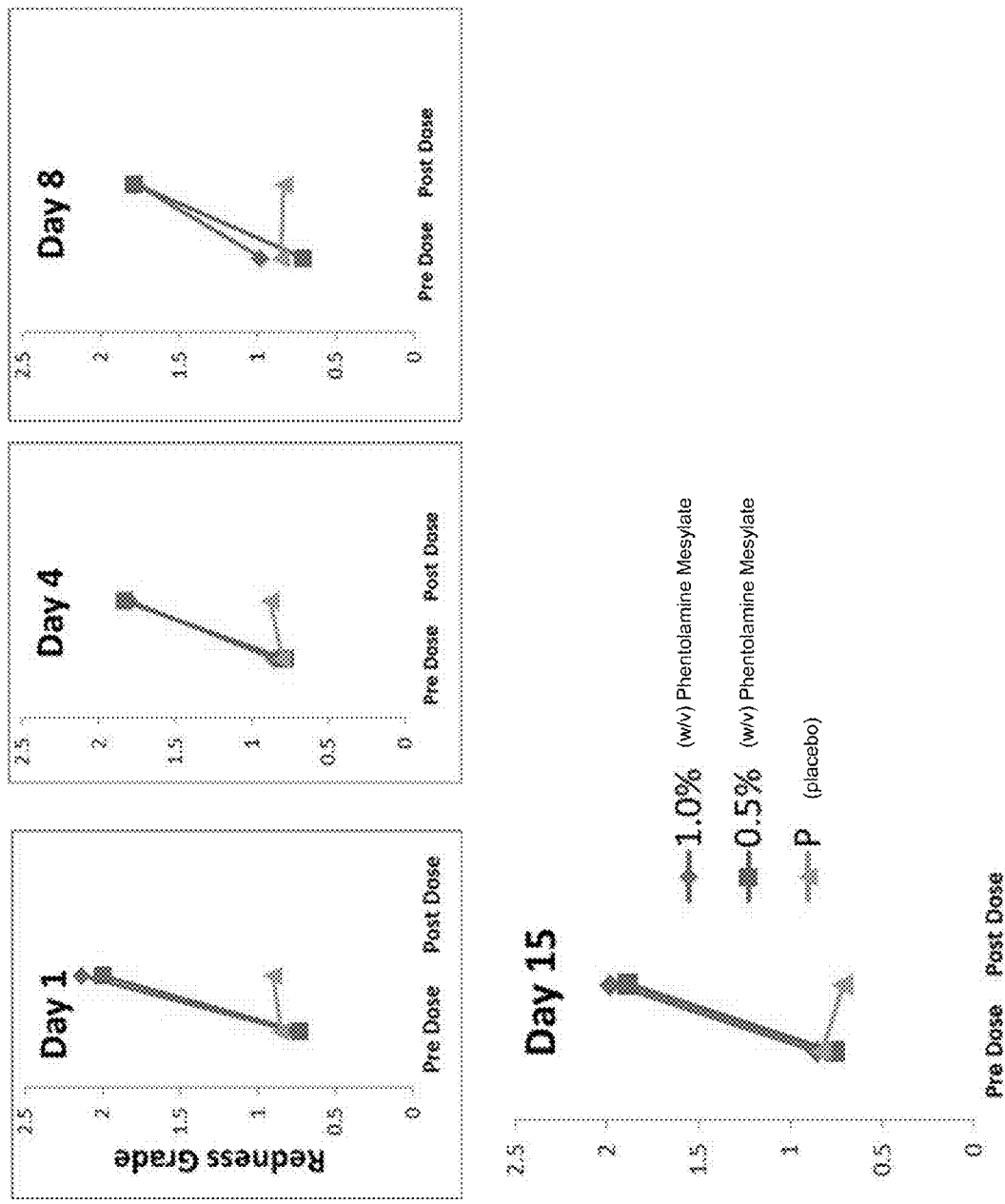
FIG. 5 depicts multiple line graphs showing eye redness in patients before and after receiving phentolamine mesylate on days, 1, 4, 8, and 15 of the study, as described in Example 1.

FIG. 5 is a line graph depicting the results from eye redness measurements. FIG. 5 shows that eye redness increases immediately after administration of the phentolamine mesylate, but that the eye redness subsides (i.e., returns to baseline) when measured prior to phentolamine mesylate administration on days 4, 8, and 15.

Figure 6:
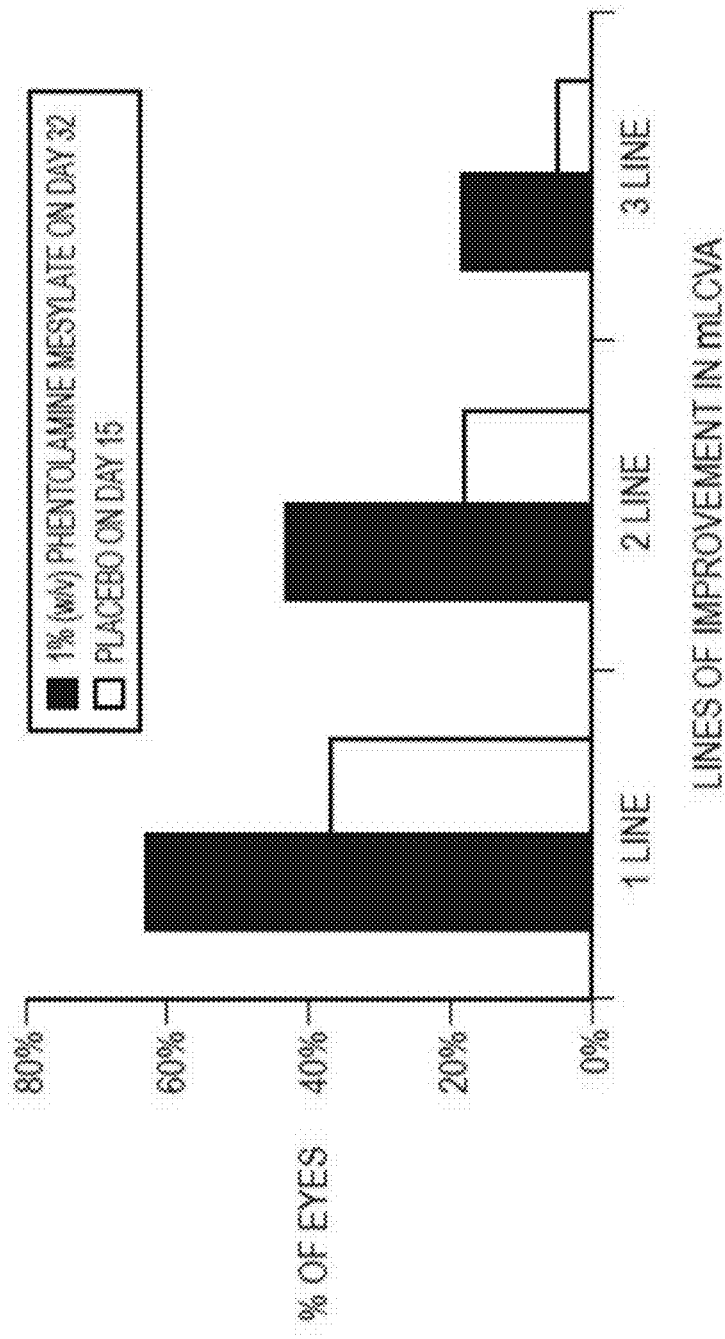
FIG. 6 is a bar graph showing the percentage of eyes with an improvement in mesopic low contrast visual acuity (mLCVA), as described in Example 1, where eyes received either placebo (P) or a 1% (w/v) phentolamine mesylate solution.
Figure 7:
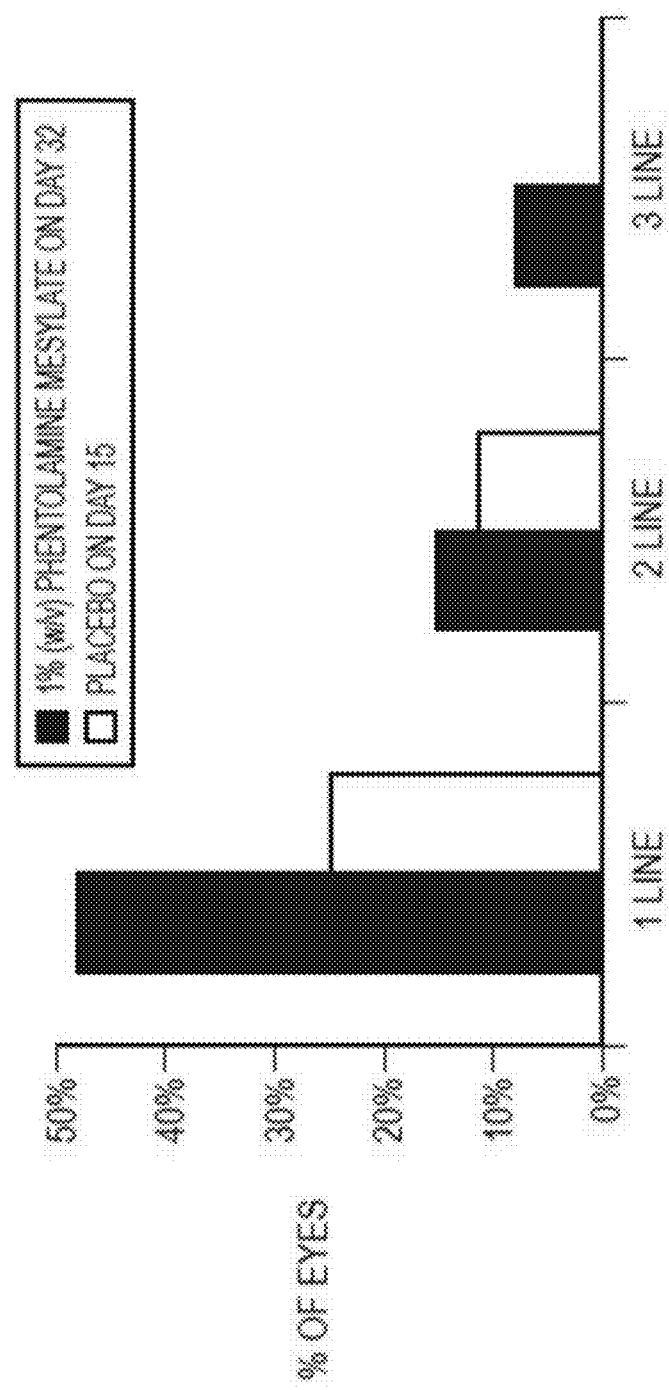
FIG. 7 is a bar graph showing the percentage of eyes with an improvement in photopic high contrast visual acuity (pHCVA), as described in Example 1, where eyes received either placebo (P) or a 1% (w/v) phentolamine mesylate solution.
Figure 8:
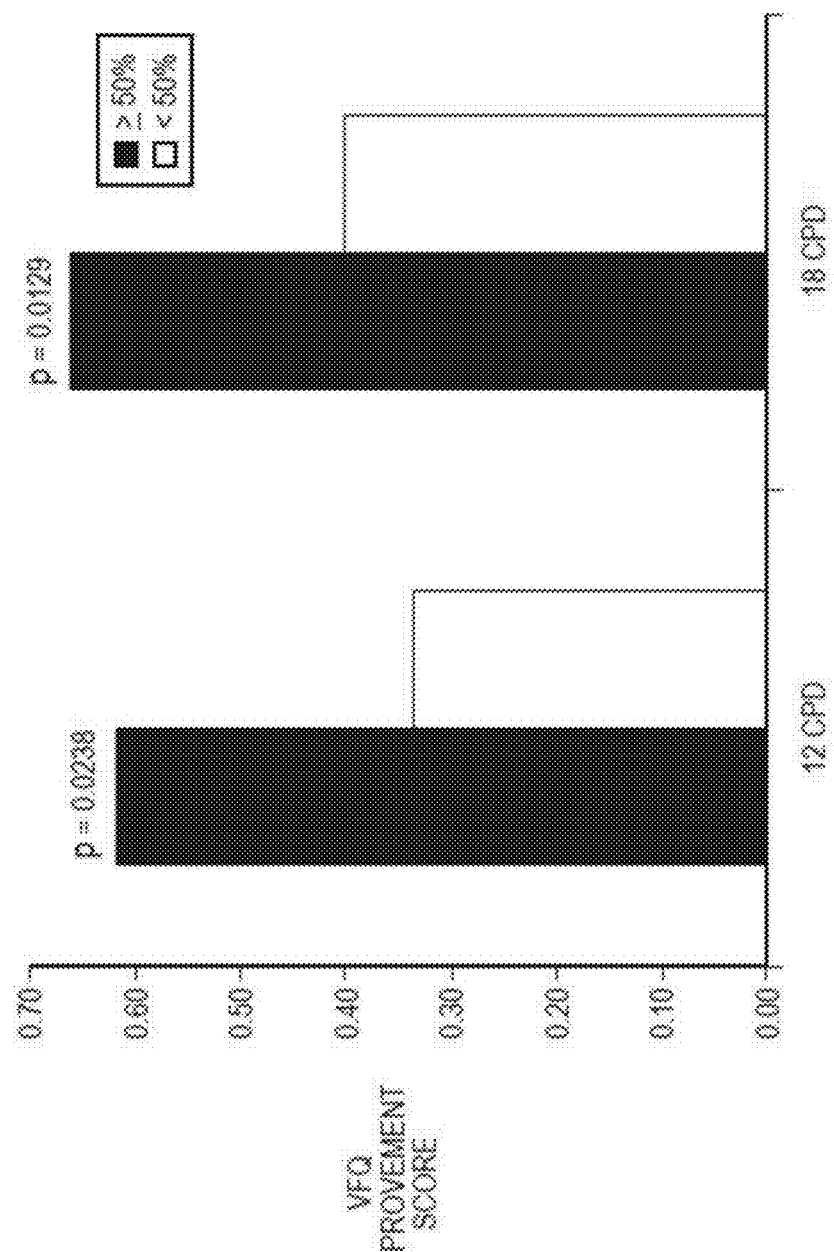
FIG. 8 is a bar graph showing mean Visual Functioning Questionnaire (VFQ) Improvement Score on day 32 of the study in subjects with ≥50% vs. <50% improvement in contrast sensitivity, as described in Example 1, where the abbreviation "CPD" refers to cycles per degree.
Figure 9:
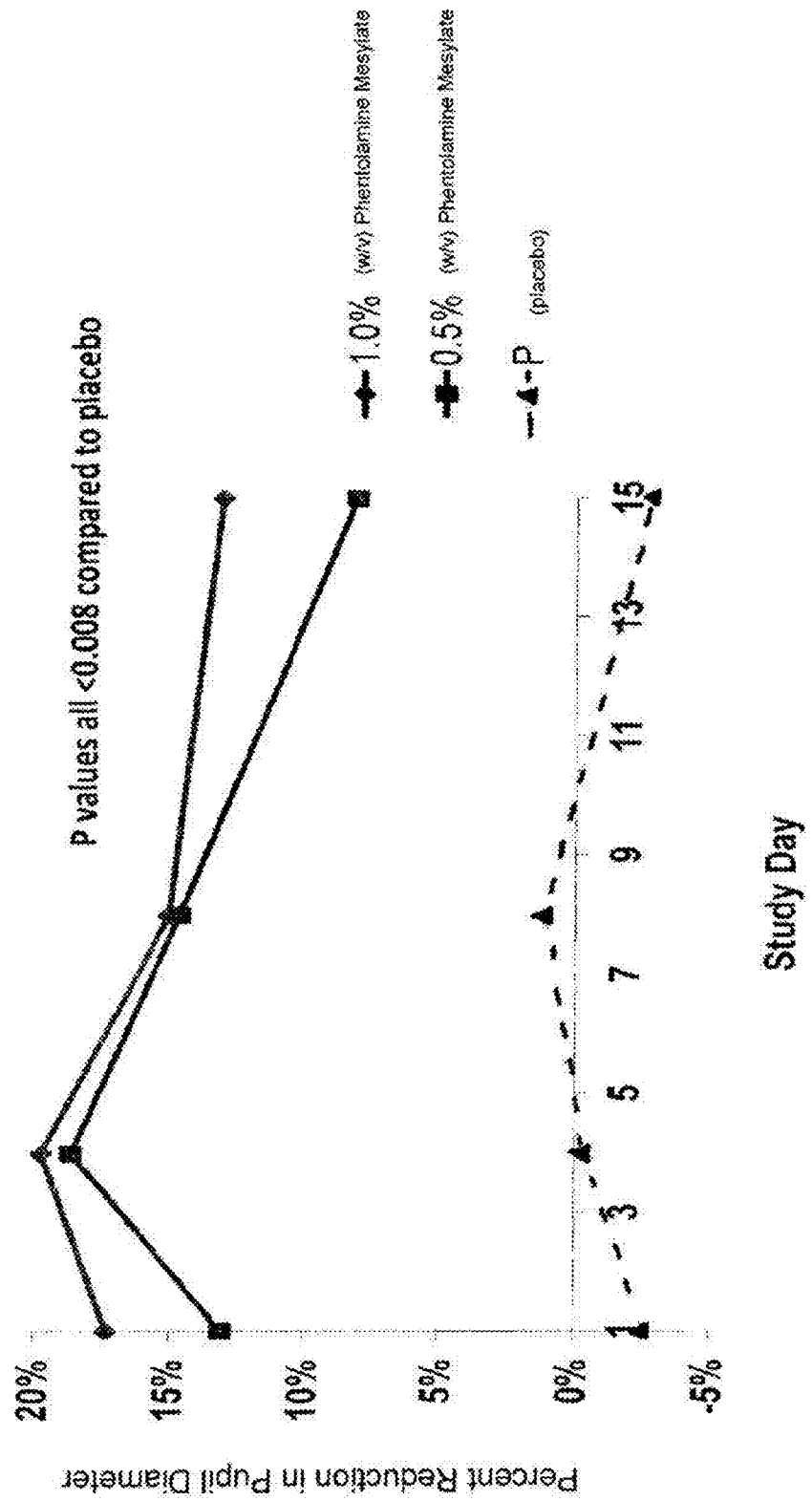
FIG. 9 is a line graph showing the reduction in pupil diameter relative to baseline after daily administration of phentolamine mesylate, as described in Example 1 where the patient's pupil diameter was measured on days 1, 4, 8, and 15 of the study two hours after administration of that day's dose.
Figure 10:
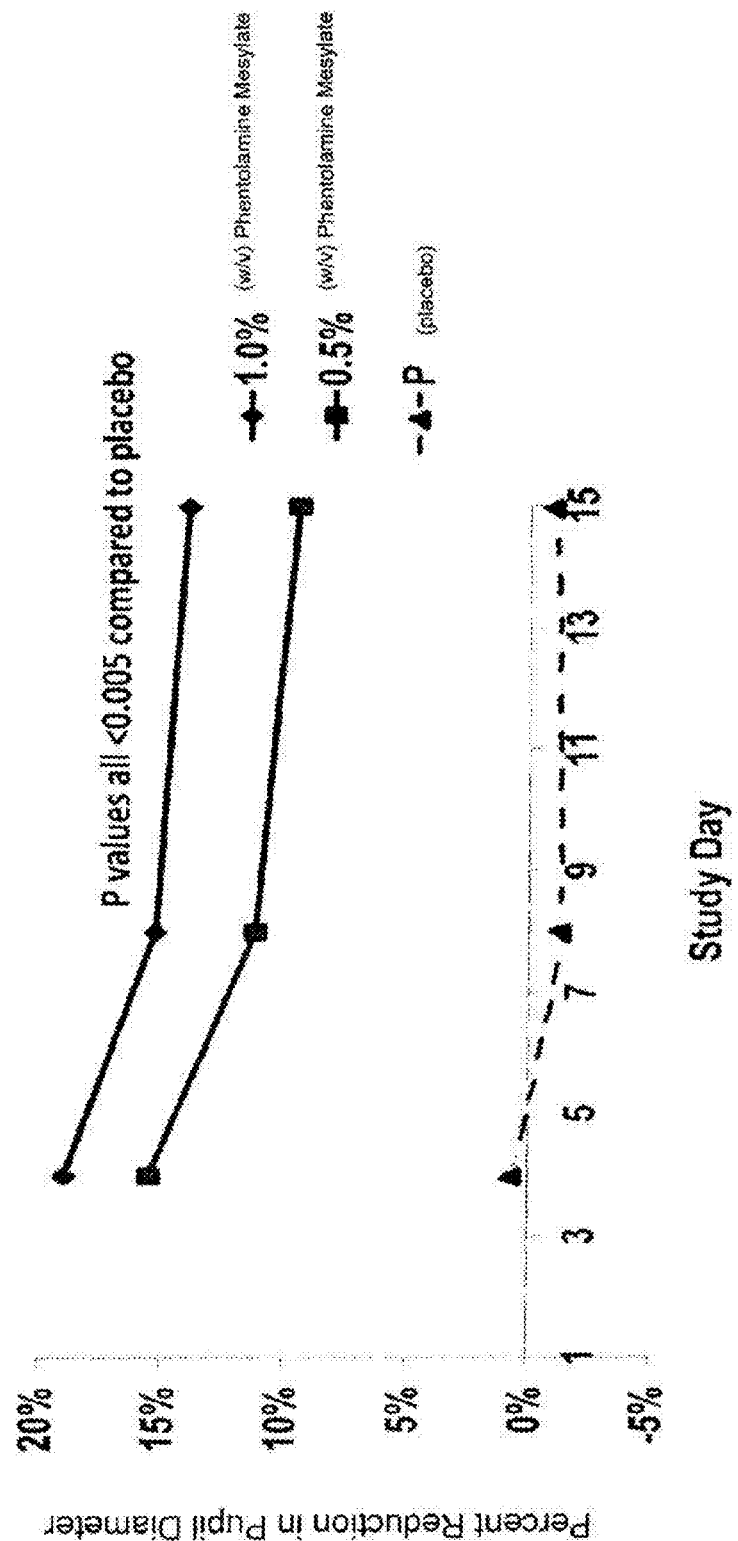
FIG. 10 is a line graph showing the reduction in pupil diameter relative to baseline prior to daily administration of phentolamine mesylate, as described in Example 1 where the patient's pupil diameter was measured on days 1, 4, 8, and 15 of the study prior to administration of that day's dose.

FIGS. 6 and 7 are bar graphs showing the percentage of eyes that demonstrated improvement in visual acuity as measured using a Snellen chart. FIG. 8 depicts bar graphs showing the mean VFQ Improvement Score on day 32 of the study in subjects with ≥50% vs. <50% improvement in contrast sensitivity. FIGS. 9 and 10 are line graphs showing the observed reduction in pupil diameter. FIG. 9 shows the reduction in pupil diameter relative to baseline when measured two hours after that day's administration of phentolamine mesylate. FIG. 10 shows the reduction in pupil diameter relative to baseline when measured prior to that day's administration of phentolamine mesylate.

Example 2

A clinical study was performed in which a phentolamine mesylate solution was administered to eyes of patients that were at least 18 years old and had a clinical history of pupil sizes of at least 7 mm in diameter under dim light conditions. The phentolamine mesylate solution contained either 0.2% (w/v) phentolamine mesylate, 0.4% (w/v) phentolamine mesylate, or 0.8% (w/v) phentolamine mesylate. Experimental procedures and results are described below.

Part I—Experimental Procedures

Sixteen patients were randomized into four groups (of four subjects each). Each group was treated on three successive study visits separated by at least 4 days with one drop of ophthalmic oxymetazoline solution (Visine LR®) in each eye followed by one drop test article in each eye. The test article was a 0.2% (w/v) phentolamine mesylate solution, 0.4% (w/v) phentolamine mesylate solution, 0.8% (w/v) phentolamine mesylate solution, or placebo. Test articles contained the designed amount of phentolamine mesylate in a solution of Tears Naturale II® (from Alcon Labs). Placebo was just Tears Naturale II® (from Alcon Labs). Tears Naturale II® (from Alcon Labs) contains Dextran 70 (0.1% by weight), Hydroxypropyl Methylcellulose 2910 (0.3% by weight), Polyquaternium-1 (0.001% by weight), potassium chloride, water (purified), sodium borate, sodium chloride, and hydrochloric acid and/or sodium hydroxide as necessary to adjust the pH. The patients' eye redness and pupil diameters were recorded at baseline (i.e., prior to treatment administration), and at 30 minutes, 1 hour, 2 hours, 4 hours, and 8 hours after administration of test articles. The incidence of any treatment-emergent adverse events was also recorded. Total study duration was approximately nine hours. Treatment group randomization schedules are provided in Table 1 below.

TABLE 1

TREATMENT GROUP RANDOMIZATION SCHEDULES

| | Visit 1 Treatment | Visit 2 Treatment | Visit 3 Treatment |
|---|---|---|---|
| Group 1 (N = 4) | 0.2% (w/v) phentolamine mesylate solution | 0.4% (w/v) phentolamine mesylate solution | 0.8% (w/v) phentolamine mesylate solution |
| Group 2 (N = 4) | 0.2% (w/v) phentolamine mesylate solution | 0.4% (w/v) phentolamine mesylate solution | placebo |
| Group 3 (N = 4) | 0.2% (w/v) phentolamine mesylate solution | placebo | 0.8% (w/v) phentolamine mesylate solution |
| Group 4 (N = 4) | placebo | 0.4% (w/v) phentolamine mesylate solution | 0.8% (w/v) phentolamine mesylate solution |

Patients were eligible for enrollment if they were (a) at least 18 years of age, and (b) had a documented pupil size in dim light of greater than 7 mm. Patients were ineligible for enrollment in the study if they met any of the following criteria: (a) had moderate to severe hypertension, (b) had a history of heart rate abnormalities, (c) had been administered any investigational drug within 14 days of screening, (d) had a known local or systemic hypersensitivity to adrenergic antagonists, or (e) had central corneal pathology.

Eye redness of patients' eyes was evaluated by the research assistant and recorded as a single integer of value 0 (no redness) to 4 (extreme redness) at baseline and each time point after treatment. Pupil diameters were measured to within 0.1 mm for each eye at baseline and each subsequent time point using a NeurOptics™ pupilometer. Monocular high contrast visual acuity was measured for each eye under photopic conditions at baseline and each subsequent time point in a darkened room using a Precision Vision™ High Contrast (100% tint) Visual Acuity Chart (Catalog #2102) backlit by the Precision Vision Illumination Box. Monocular low contrast visual acuity was measured for each eye under photopic conditions at baseline and each subsequent time point in a darkened room using a Precision Vision™ Low Contrast (5% tint) Visual Acuity Chart (Catalog #2186) backlit by the Precision Vision Illumination Box. Effect of treatment on glare was assessed using an experimental test method consisting of a panel with a high wattage central light emitting diode (LED) and a set of 7 lower wattage red LEDs radiating horizontally and vertically from the central light.

Comparisons of changes in mean values within treatment groups were tested for significance using two-tailed paired two sample t-tests with a threshold for significance set at p<0.01 (Bonferroni Correction for multiple paired t-tests). Differences between treatment groups with respect to mean values for pupil size over the course of the study were tested for significance using repeated measure ANOVA (which discards data from subjects lacking any data points). Differences in mean eye redness between treatment groups were evaluated using Kruskal-Wallis nonparametric testing. Differences in means between treatment groups at individual time points were tested for significance using one-way ANOVA. If one-way ANOVA showed significance at a given time point, ad hoc Fisher's testing was performed to identify significant differences between individual group means.

Part II—Results

Fifteen of 16 patients completed the study. One patient randomized to Group 3 completed only two of three clinic visits, missing the 0.8% (w/v) phentolamine mesylate dose. The results of pupil measurements, visual acuity testing, and eye redness are described below.

Pupil Measurements

One criterion for entrance into the study was historical documentation of a pupil size >7 mm when measured under dim light conditions. Table 2 provides the mean pupil diameters, standard deviation of pupil diameters, and the observed range of diameters recorded immediately prior to administration of each treatment.

TABLE 2

BASELINE PUPIL MEASURES

| Pupil Variable | Placebo | 0.2% (w/v) Phentolamine Mesylate | 0.4% (w/v) Phentolamine Mesylate | 0.8% (w/v) Phentolamine Mesylate |
|---|---|---|---|---|
| Sample Size[a] | 24 | 24 | 24 | 22[b] |
| Mean Diameter (mm) | 7.8 | 7.8 | 7.7 | 8.0 |
| Standard Deviation (mm) | 0.6 | 0.9 | 0.7 | 1.1 |
| Range (mm) | 6.5-8.7 | 5.2-8.8 | 5.8-8.6 | 4.6-9.3 |

[a]measurements from each pupil treated separately
[b]one subject missed the 0.8% phentolamine dosing visit Average baseline pupil diameters were comparable across all four treatment groups, with observed differences in means (Table 2) not statistically significant (P=0.766). Of the 94 baseline pupil diameters collected during the study, there were twelve instances (representing 3 subjects; Table 3) in which baseline pupil diameters were less than the inclusion criterion of 7 mm. Baseline pupil diameters less than 7 mm were evenly distributed between treatment groups (2, 3, 4, and 3 pupils in Placebo, 0.2%, 0.4%, and 0.8% (w/v) phentolamine mesylate treatment groups, respectively).

TABLE 3

SUBJECTS WITH BASELINE PUPIL DIAMETERS LESS THAN 7 MM

| | Subject 2 | | Subject 6 | | Subject 16 | |
|---|---|---|---|---|---|---|
| Study Visit | Right Pupil (mm) | Left Pupil (mm) | Right Pupil (mm) | Left Pupil (mm) | Right Pupil (mm) | Left Pupil (mm) |
| 1 | 6.7 | 7.1 | 7 | 7 | 5.8 | 5.7 |
| 2 | 6.7 | 6.5 | 6.8 | 6.3 | 6.3 | 5.8 |
| 3 | 7.9 | 8.2 | 7.4 | 6.7 | 5.5 | 4.6 |

For all study groups, mean pupil diameters were relatively unchanged at 30 minutes after treatment. By one hour post treatment, mean pupil diameters were lower (P=0.47) for phentolamine-treated subjects. Mean pupil diameters for subjects receiving placebo were relatively constant for the 8 hours of post-treatment observation.

TABLE 4

MEAN PUPIL DIAMETERS DURING THE STUDY

| Treatment Group[a] | Baseline | 30 min | 1 hour | 2 hours | 4 hours | 8 hours |
|---|---|---|---|---|---|---|
| Placebo | | | | | | |
| Mean Diameter (mm) | 7.83 | 7.87 | 7.80 | 7.93 | 7.87 | 8.08[b] |
| Standard Deviation | 0.61 | 0.81 | 0.79 | 0.60 | 0.58 | 0.75 |
| Minimum (mm) | 6.5 | 5.5 | 5.9 | 6.5 | 6.8 | 6.5 |
| Maximum (mm) | 8.7 | 9.0 | 9.2 | 9.0 | 9.0 | 9.3 |
| 0.2% (w/v) Phentolamine Mesylate | | | | | | |
| Mean Diameter (mm) | 7.78 | 7.74 | 7.54 | 7.01[c] | 7.30[d] | 7.18 |
| Standard Deviation | 0.88 | 1.02 | 1.02 | 0.82 | 0.51 | 0.90 |
| Minimum (mm) | 5.2 | 5.1 | 4.9 | 4.7 | 6.3 | 4.7 |
| Maximum (mm) | 8.8 | 9.2 | 8.9 | 8.4 | 8.0 | 8.5 |
| 0.4% (w/v) Phentolamine Mesylate | | | | | | |
| Mean Diameter (mm) | 7.71 | 7.72 | 7.41 | 7.05 | 7.01 | 7.01 |
| Standard Deviation | 0.71 | 0.81 | 0.77 | 0.84 | 0.92 | 0.97 |
| Minimum (mm) | 5.8 | 5.6 | 5.5 | 5.0 | 5.0 | 4.8 |
| Maximum (mm) | 8.6 | 8.8 | 8.3 | 8.4 | 8.1 | 8.6 |
| 0.8% (w/v) Phentolamine Mesylate [e] | | | | | | |
| Mean Diameter (mm) | 7.96 | 7.87 | 7.69 | 7.30 | 7.32 | 7.40 |
| Standard Deviation | 1.10 | 0.97 | 0.97 | 0.99 | 0.99 | 0.99 |
| Minimum (mm) | 4.6 | 5.2 | 5.1 | 4.7 | 5.5 | 4.7 |
| Maximum (mm) | 9.3 | 9.2 | 9.1 | 8.7 | 8.6 | 8.7 |

[a]24 pupils per sample except where noted
[b]20 pupils; 8 hour data for subjects 2 and 11, visit 2, were not recorded
[c]22 pupils; 2 hour data from subject 7, visit 1 not recorded
[d]22 pupils; 4 hour data from subject 16, visit 1 not recorded
[e] 22 pupils at each time point, subject 16 missed visit 3

Repeated measures ANOVA showed a significant (p<0.001) difference between treatment groups with respect to pupil diameter over the course of the study. Significant differences in mean pupil diameters between treatment were identified by one-way ANOVA at 2 hours (p=0.0006), 4 hours (p=0.0027) and 8 hours (p=0.0016) after treatment. Ad hoc Fisher's tests of significance between individual group means demonstrated significant differences in mean pupil diameters of subjects treated with any concentration of phentolamine mesylate when compared to placebo at 2, 4 and 8 hours (Table 5). In contrast, there were no statistically significant differences in mean pupil diameters observed between different doses of phentolamine at any time point.

TABLE 5

SIGNIFICANCE OF DIFFERENCES
BETWEEN MEAN PUPIL DIAMETERS

| Treatment Comparison | 2 hours | 4 hours | 8 hours |
|---|---|---|---|
| Placebo vs. 0.2% (w/v) Phentolamine Mesylate | P = 0.0003 | P = 0.0147 | P = 0.0018 |
| Placebo vs. 0.4% (w/v) Phentolamine Mesylate | P = 0.0003 | P = 0.0002 | P = 0.0002 |
| Placebo vs. 0.8% (w/v) Phentolamine Mesylate | P = 0.0110 | P = 0.0200 | P = 0.0199 |

* Fisher's Ad Hoc test of means for time points previously shown to be significant by One-Way ANOVA For all treatment groups, mean pupil diameters were relatively unchanged from baseline at 30 minutes after treatment (Table 6). By one hour post treatment, change from baseline in mean pupil diameters was significant (p<0.01) for subjects treated with 0.2% (w/v), 0.4% (w/v), and 0.8% (w/v) phentolamine mesylate. Mean pupil diameters did not significantly change from baseline for subjects receiving placebo over the 8 hours of post-treatment observation.

Differences in mean pupil diameters of treatment groups are expressed as mean changes in diameter from baseline in Table 6. When mean changes in pupil diameters from baseline are evaluated as a function of time, it is apparent that those subjects receiving phentolamine mesylate experienced significant reductions in pupil size over the course of the study.

TABLE 6

MEAN PUPIL DIAMETER CHANGES
FROM BASELINE OVER TIME

| Treatment Group | 30 min | 1 hour | 2 hours | 4 hours | 8 hours |
|---|---|---|---|---|---|
| Placebo | | | | | |
| Mean Change (mm) | 0.04 | −0.03 | 0.10 | 0.04 | 0.12 |
| Standard Deviation | 0.32 | 0.36 | 0.34 | 0.51 | 0.35 |
| Sample Size (pupils) | 24 | 24 | 24 | 24 | 20 |
| P- value$^a$ | 0.57 | 0.66 | 0.15 | 0.72 | 0.15 |
| 0.2% (w/v) Phentolamine Mesylate | | | | | |
| Mean Change (mm) | −0.04 | −0.24 | −0.75 | −0.69 | −0.59 |
| Standard Deviation | 0.33 | 0.37 | 0.51 | 0.49 | 0.62 |
| Sample Size (pupils) | 24 | 24 | 22 | 22 | 24 |
| P- value$^a$ | 0.58 | <0.005 | <0.001 | <0.001 | <0.001 |
| 0.4% (w/v) Phentolamine Mesylate | | | | | |
| Mean Change (mm) | 0.00 | −0.29 | −0.64 | −0.74 | −0.74 |
| Standard Deviation | 0.40 | 0.33 | 0.46 | 0.45 | 0.47 |
| Sample Size (pupils) | 22 | 22 | 22 | 22 | 22 |
| P- value$^a$ | 0.86 | <0.001 | <0.001 | <0.001 | <0.001 |
| 0.8% (w/v) Phentolamine Mesylate | | | | | |
| Mean Change (mm) | −0.10 | −0.27 | −0.66 | −0.64 | −0.56 |
| Standard Deviation | 0.31 | 0.43 | 0.44 | 0.61 | 0.43 |
| Sample Size (pupils) | 22 | 22 | 22 | 22 | 22 |
| P- value$^a$ | 0.16 | <0.007 | <0.001 | <0.001 | <0.001 |

$^a$Two-sided paired two-sample t-test. P < 0.01 is significant by Bonferroni correction Visual Acuity Mean values for best corrected high-contrast visual acuity were not statistically significantly different between treatment groups at baseline, with Log Mar values ranging from 0.04 to 0.08 (Table 7), equivalent of a range of 20/16 to 20/18 vision. Despite the observation that mean baseline high contrast visual acuities were above "normal" (i.e., better than 20/20) for all treatment groups, mean acuity increased for all groups 30 minutes after treatment and mean acuities remained elevated above baseline throughout the 8-hour observation period (Table 7). Two-sided paired two-sample t-tests of visual acuities compared to baseline showed that all treatment groups (including placebo) with the exception of 0.8% (w/v) phentolamine mesylate had at least one time point after treatment in which visual acuities were significantly elevated relative to baseline (bolded P values of Table 7).

TABLE 7

EFFECTS ON HIGH CONTRAST VISUAL ACUITY

| Treatment Group$^a$ | Baseline | 30 Min | 1 hour | 2 hour | 4 hours | 8 hours |
|---|---|---|---|---|---|---|
| Placebo | | | | | | |
| Mean acuity (LogMar) | 0.08 | 0.10 | 0.13 | 0.12 | 0.12 | 0.11$^b$ |
| Standard Deviation | 0.11 | 0.09 | 0.08 | 0.09 | 0.07 | 0.08 |
| Minimum (LogMar) | −0.15 | −0.10 | −0.02 | −0.10 | −0.02 | −0.10 |
| Maximum (LogMar) | 0.26 | 0.26 | 0.30 | 0.30 | 0.22 | 0.22 |
| P- value$^c$ | | 0.612 | 0.020 | 0.003 | 0.014 | 0.087 |
| 0.2% (w/v) Phentolamine Mesylate | | | | | | |
| Mean acuity (LogMar) | 0.04 | 0.05 | 0.08 | 0.08 | 0.09 | 0.08 |
| Standard Deviation | 0.13 | 0.14 | 0.12 | 0.12 | 0.12 | 0.13 |
| Minimum (LogMar) | −0.32 | −0.32 | −0.20 | −0.22 | −0.20 | −0.32 |
| Maximum (LogMar) | 0.22 | 0.22 | 0.22 | 0.26 | 0.22 | 0.22 |
| P- value$^c$ | | 0.612 | 0.020 | 0.003 | 0.001 | 0.002 |
| 0.4% (w/v) Phentolamine Mesylate | | | | | | |
| Mean acuity (LogMar) | 0.09 | 0.12 | 0.11 | 0.14 | 0.15 | 0.13 |
| Standard Deviation | 0.11 | 0.09 | 0.11 | 0.10 | 0.09 | 0.11 |

TABLE 7-continued

EFFECTS ON HIGH CONTRAST VISUAL ACUITY

| Treatment Group[a] | Baseline | 30 Min | 1 hour | 2 hour | 4 hours | 8 hours |
|---|---|---|---|---|---|---|
| Minimum (LogMar) | −0.24 | −0.20 | −0.20 | −0.10 | −0.11 | −0.18 |
| Maximum (LogMar) | 0.22 | 0.22 | 0.26 | 0.30 | 0.30 | 0.30 |
| P- value[c] | | 0.002 | 0.147 | 0.001 | 0.001 | 0.010 |
| 0.8% (w/v) Phentolamine Mesylate [d] | | | | | | |
| Mean acuity (LogMar) | 0.06 | 0.11 | 0.12 | 0.12 | 0.12 | 0.13 |
| Standard Deviation | 0.15 | 0.11 | 0.11 | 0.12 | 0.14 | 0.13 |
| Minimum (LogMar) | −0.41 | −0.16 | −0.10 | −0.16 | −0.20 | −0.20 |
| Maximum (LogMar) | 0.22 | 0.22 | 0.26 | 0.30 | 0.30 | 0.30 |
| P- value[c] | | 0.126 | 0.061 | 0.043 | 0.054 | 0.039 |

[a]12 subjects, 24 eyes per treatment group except where noted
[b]Mean of 10 subjects, 20 eyes
[c]Two-sided paired two-sample t-test compared to baseline. P < 0.01 is significant by Boneferroni correction
[d] Mean of 11 subjects, 22 eyes A trend (P=0.16) towards phentolamine dose-proportionality in high contrast visual acuity improvement was observed by repeated measures ANOVA. This trend in high contrast vision improvement was modest, with a maximal mean increase of 0.06 Log Mar at 4 and 8 hours for subjects treated with 0.8% phentolamine, roughly equating to an improvement in vision of 3 letters on a Snellen chart.

Mean values for best corrected low contrast visual acuity were not statistically significantly different between treatment groups at baseline, with Log Mar values ranging from −0.34 to −0.28 (Table 8), roughly equivalent to a range of 20/38 to 20/44 vision. Mean low contrast acuity increased for all groups 30 minutes after treatment (Table 8). Beyond 30 minutes, there was strong evidence of phentolamine dose-proportionality with respect to improvement in mean low contrast visual acuity. Treatment with 0.8% (w/v) phentolamine mesylate resulted in significant increases in mean low contrast acuity at all post-treatment time points compared to baseline, as did treatment with 0.4% (w/v) phentolamine mesylate at 1, 2, 4, and 8 hours post treatment (two-sided paired two-sample t-test; bolded P values of Table 8).

TABLE 8

EFFECTS ON LOW CONTRAST VISUAL ACUITIES

| Treatment Group[a] | Baseline | 30 min | 1 hour | 2 hours | 4 hours | 8 hours |
|---|---|---|---|---|---|---|
| Placebo | | | | | | |
| Mean acuity (LogMar) | −0.29 | −0.28 | −0.27 | −0.27 | −0.25 | −0.30[b] |
| Standard Deviation | 0.13 | 0.10 | 0.11 | 0.10 | 0.09 | 0.07 |
| Minimum (LogMar) | −0.64 | −0.50 | −0.60 | −0.50 | −0.40 | −0.42 |
| Maximum (LogMar) | −0.11 | −0.11 | −0.11 | −0.10 | −0.10 | −0.20 |
| P value[c] | | 0.230 | 0.189 | 0.192 | 0.022 | 0.710 |
| 0.2% (w/v) Phentolamine Mesylate | | | | | | |
| Mean acuity (LogMar) | −0.34[d] | −0.35 | −0.32 | −0.32 | −0.30 | −0.30[e] |
| Standard Deviation | 0.18 | 0.19 | 0.18 | 0.17 | 0.20 | 0.19 |
| Minimum (LogMar) | −0.80 | −0.78 | −0.80 | −0.74 | −0.76 | −0.72 |
| Maximum (LoeMar) | −0.06 | −0.10 | −0.08 | −0.11 | 0.00 | −0.08 |
| P value[c] | | 0.724 | 0.060 | 0.198 | 0.111 | 0.026 |
| 0.4% (w/v) Phentolamine Mesylate | | | | | | |
| Mean acuity (LogMar) | −0.28 | −0.24 | −0.24 | −0.22 | −0.20 | −0.22 |
| Standard Deviation | 0.13 | 0.15 | 0.17 | 0.14 | 0.16 | 0.15 |
| Minimum (LogMar) | −0.74 | −0.70 | −0.78 | −0.64 | −0.70 | −0.64 |
| Maximum (LogMar) | −0.10 | 0.00 | −0.04 | 0.00 | 0.00 | 0.00 |
| P value[c] | | 0.011 | 0.006 | 0.001 | 0.001 | 0.001 |
| 0.8% (w/v) Phentolamine Mesylate [e] | | | | | | |
| Mean acuity (LogMar) | −0.34 | −0.28 | −0.25 | −0.22 | −0.22 | −0.25 |
| Standard Deviation | 0.16 | 0.16 | 0.15 | 0.15 | 0.17 | 0.19 |
| Minimum (LogMar) | −0.78 | −0.76 | −0.62 | −0.60 | −0.70 | −0.78 |

TABLE 8-continued

EFFECTS ON LOW CONTRAST VISUAL ACUITIES

| Treatment Group[a] | Baseline | 30 min | 1 hour | 2 hours | 4 hours | 8 hours |
|---|---|---|---|---|---|---|
| Maximum (LogMar) | −0.11 | −0.02 | 0.00 | 0.00 | 0.00 | 0.00 |
| P value[c] | | 0.001 | 0.001 | 0.001 | 0.001 | 0.001 |

[b]12 subjects, 24 eyes per treatment group except where noted
[c]Mean of 10 subjects, 20 eyes
[d]Two-sided paired two-sample t-test compared to baseline. P < 0.01 is significant by Bonferroni correction
[e]Mean of 12 subjects, 23 eyes (one entry missing on CRF)
f - Mean of 11 subjects, 22 eyes Statistically-significant (P=0.0091) different changes in low contrast visual acuity between groups were observed in the study by repeated measures ANOVA). One-way ANOVA at each time point identified significant differences between mean low contrast visual acuities at 2 hours post-dosing, and ad hoc Fisher's testing identified significant differences between 0.2% (w/v) phentolamine treatment and both 0.4% (w/v) phentolamine mesylate and 0.8% (w/v) phentolamine mesylate treatment (P<0.05). The magnitude of low contrast vision improvement was relatively modest, with a maximal mean increase of 0.12 Log Mar at 2 hours for subjects treated with 0.8% (w/v) phentolamine mesylate roughly equating to an improvement in vision of 6 letters on a Snellen chart.

Eye Redness

Figure 12:
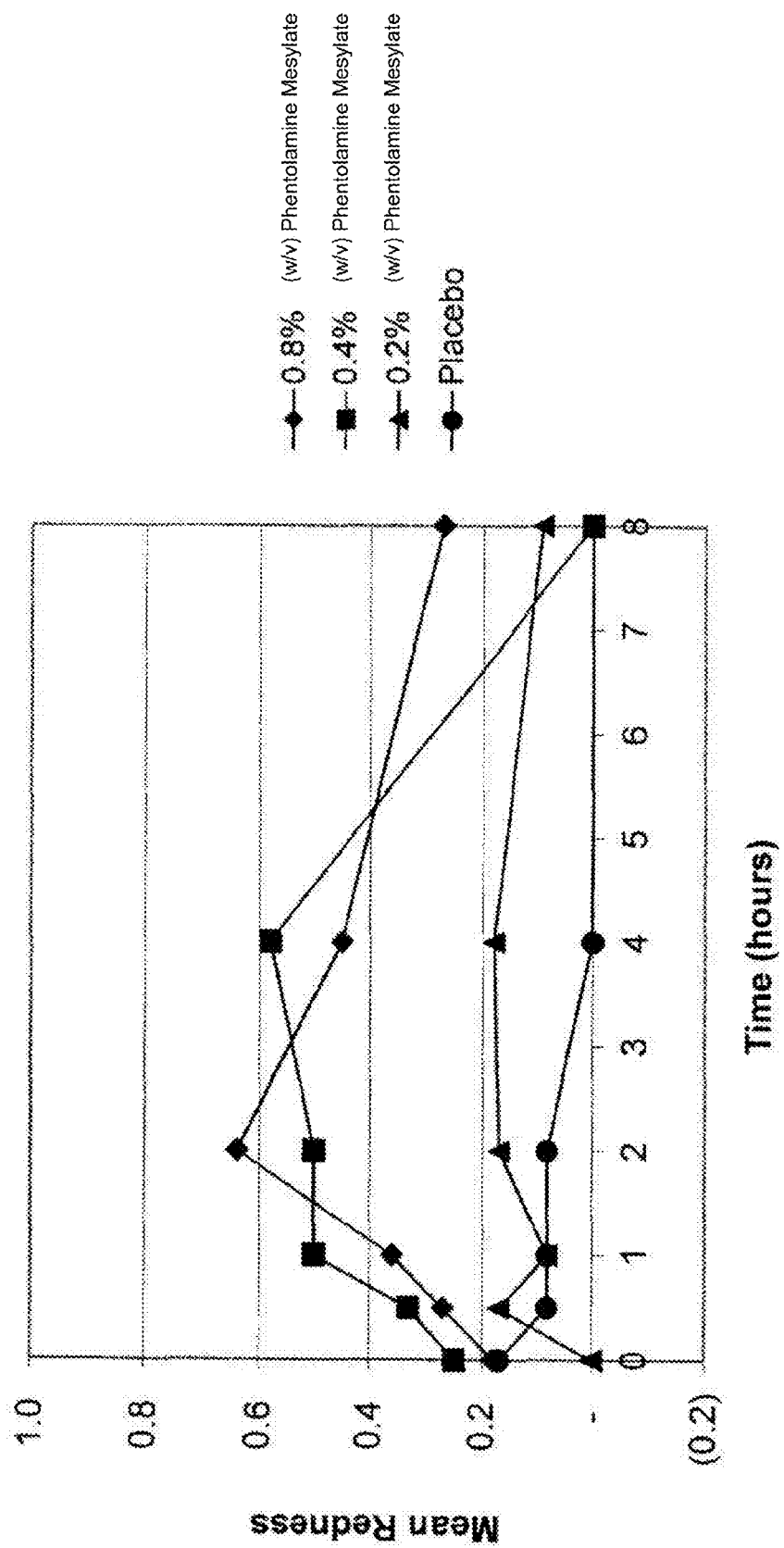
FIG. 12 is a line graph showing eye redness score for patients 0.5, 1, 2, 4, and 8 hours after receiving placebo or a phentolamine mesylate solution, as described in Example 2.

Eye redness was recorded on an integer scale of 0 (least) to 4 (most) redness at each time point collected. Mean eye redness at baseline (Table 9) was not statistically different between treatment groups (P=0.6625; Kruskal-Wallis non-parametric analysis). Over the course of the study, mean eye redness for subjects treated with 0.2% (w/v) phentolamine mesylate did not differ from placebo. Subjects treated with either 0.4% (w/v) or 0.8% (w/v) phentolamine mesylate experienced a modest increase in eye redness at 2 and 4 hours post treatment, which regressed by 8 hours. Differences in mean eye redness between treatment groups were only significant (P=0.0152; Kruskal-Wallis nonparametric analysis) at 4 hours post treatment. FIG. 12 is a line graph showing eye redness as a function of time, whereby eye redness returns to baseline within 8 hours after administration of phentolamine mesylate.

TABLE 9

MEAN EYE REDNESS SCORES

| Treatment Group[a] | Baseline | 30 min | 1 hour | 2 hours | 4[b] hours | 8 hours |
|---|---|---|---|---|---|---|
| Placebo | | | | | | |
| Mean Score | 0.17 | 0.08 | 0.08 | 0.08 | 01[b] | 0[b] |
| Standard Deviation | 0.39 | 0.29 | 0.29 | 0.29 | 0 | 0 |
| Range | 0-1 | 0-1 | 0-1 | 0-1 | 0-0 | 0-0 |
| 0.2% (w/v) Phentolamine Mesylate | | | | | | |
| Mean Score | 0.00 | 0.17 | 0.08 | 0.17 | 0.18[b] | 0.09[b] |
| Standard Deviation | 0.00 | 0.39 | 0.29 | 0.39 | 0.40 | 0.30 |
| Range | 0-1 | 0-1 | 0-1 | 0-1 | 0-1 | 0-1 |
| 0.4% (w/v) Phentolamine Mesylate [c] | | | | | | |
| Mean Score | 0.25 | 0.33 | 0.50 | 0.50 | 0.58 | 0.00 |
| Standard Deviation | 0.45 | 0.49 | 0.67 | 0.67 | 0.67 | 0.00 |

TABLE 9-continued

MEAN EYE REDNESS SCORES

| Treatment Group[a] | Baseline | 30 min | 1 hour | 2 hours | 4[b] hours | 8 hours |
|---|---|---|---|---|---|---|
| Range | 0-1 | 0-1 | 0-2 | 0-2 | 0-2 | 0-0 |
| 0.8% (w/v) Phentolamine Mesylate | | | | | | |
| Mean Score | 0.18 | 0.27 | 0.36 | 0.64 | 0.45 | 0.27 |
| Standard Deviation | 0.40 | 0.47 | 0.67 | 1.03 | 0.52 | 0.47 |
| Range | 0-1 | 0-1 | 0-2 | 0-3 | 0-1 | 0-1 |

[a]12 subjects per group except where noted
[b]Significant (P = 0.0152) differences between groups by Kruskal-Wallis nonparametric analysis
[c] data from 11 subjects

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

I claim:

1. A method of improving visual performance in a patient while minimizing eye redness during the patient's waking hours, comprising administering to an eye of a patient once per day within 1 hour of the patient's bedtime for at least five consecutive days a daily dosage of phentolamine or a pharmaceutically acceptable salt thereof sufficient to provide improved visual performance for at least twenty hours, wherein the patient experiences an increase in eye redness of no more than two grades measured using the CCLRU Redness Grading Scale during the patient's waking hours compared to the patient's level of eye redness without receiving said dosage; wherein the daily dosage is an ophthalmic solution comprising water, a polyol, and phentolamine or a pharmaceutically acceptable salt thereof.

2. The method of claim 1, wherein the improvement in visual performance is improved contrast sensitivity.

3. A method of reducing pupil diameter in a patient while minimizing eye redness during the patient's waking hours, comprising administering to an eye of a patient once per day at or near the bedtime of the patient for at least five consecutive days a daily dosage of phentolamine or a pharmaceutically acceptable salt thereof sufficient to reduce pupil diameter for at least twenty hours, wherein the patient experiences an increase in eye redness of no more than two grades measured using the CCLRU Redness Grading Scale during the patient's waking hours compared to the patient's level of eye redness without receiving said dosage; wherein the daily dosage is an ophthalmic solution comprising water, a polyol, and phentolamine or a pharmaceutically acceptable salt thereof.

4. The method of claim 3, wherein the reduction in pupil diameter under mesopic conditions is at least 5% compared to the pupil diameter of the patient under the same mesopic conditions but not having received said dosage.

5. The method of claim 3, wherein the reduction in pupil diameter under mesopic conditions is at least 10% compared to the pupil diameter of the patient under the same mesopic conditions but not having received said dosage.

6. The method of claim 3, wherein the patient experiences a reduction in pupil diameter of at least 0.5 mm when measured under mesopic conditions relative to the diameter of the patient's pupil under the same mesopic conditions but not having received said dosage.

7. A method of reducing an aberrant focus of scattered light rays in a patient's eye while minimizing eye redness during the patient's waking hours, comprising administering to an eye of a patient once per day at or near the bedtime of the patient for at least five consecutive days a daily dosage of phentolamine or a pharmaceutically acceptable salt thereof sufficient to reduce aberrant focus of scattered light rays in a patient's eye for at least twenty hours, wherein the patient experiences an increase in eye redness of no more than two grades measured using the CCLRU Redness Grading Scale during the patient's waking hours compared to the patient's level of eye redness without receiving said dosage; wherein the daily dosage is an ophthalmic solution comprising water, a polyol, and phentolamine or a pharmaceutically acceptable salt thereof.

8. The method of claim 7, wherein the method results in an improvement in visual acuity characterized by at least a one-line improvement in the patient's vision measured using a Snellen chart.

9. The method of claim 2, wherein the daily dosage is an aqueous ophthalmic solution free of a chelating agent, comprising:
(a) about 0.5% (w/v) to about 2% (w/v) of phentolamine mesylate;
(b) about 1% (w/v) to about 6% (w/v) of at least one polyol compound selected from the group consisting of is mannitol, glycerol, and propylene glycol;
(c) about 1 mM to about 6 mM of an alkali metal acetate; and
(d) water;
wherein the solution has a pH in the range of 4.5 to 5.5 and does not contain a chelating agent.

10. The method of claim 2, wherein the daily dosage is an aqueous ophthalmic solution free of a chelating agent, comprising:
(a) about 0.5% (w/v) to about 2% (w/v) of phentolamine mesylate;
(b) about 3% (w/v) to about 5% (w/v) of mannitol;
(c) about 2 mM to about 4 mM of sodium acetate; and
(d) water;
wherein the solution has a pH in the range of 4.6 to 5.2 and does not contain a chelating agent.

11. The method of claim 2, wherein the daily dosage is an aqueous ophthalmic solution free of a chelating agent, comprising:
(a) about 0.5% (w/v) to about 1% (w/v) of phentolamine mesylate;
(b) about 4% mannitol;
(c) about 3 mM sodium acetate; and
(d) water;
wherein the solution has a pH in the range of 4.6 to 5.2 and does not contain a chelating agent.

12. The method of claim 3, wherein the daily dosage is an aqueous ophthalmic solution free of a chelating agent, comprising:
(a) about 0.5% (w/v) to about 2% (w/v) of phentolamine mesylate;
(b) about 1% (w/v) to about 6% (w/v) of at least one polyol compound selected from the group consisting of is mannitol, glycerol, and propylene glycol;
(c) about 1 mM to about 6 mM of an alkali metal acetate; and
(d) water;
wherein the solution has a pH in the range of 4.5 to 5.5 and does not contain a chelating agent.

13. The method of claim 3, wherein the daily dosage is an aqueous ophthalmic solution free of a chelating agent, comprising:
(a) about 0.5% (w/v) to about 2% (w/v) of phentolamine mesylate;
(b) about 3% (w/v) to about 5% (w/v) of mannitol;
(c) about 2 mM to about 4 mM of sodium acetate; and
(d) water;
wherein the solution has a pH in the range of 4.6 to 5.2 and does not contain a chelating agent.

14. The method of claim 3, wherein the daily dosage is an aqueous ophthalmic solution free of a chelating agent, comprising:
(a) about 0.5% (w/v) to about 1% (w/v) of phentolamine mesylate;
(b) about 4% mannitol;
(c) about 3 mM sodium acetate; and
(d) water;
wherein the solution has a pH in the range of 4.6 to 5.2 and does not contain a chelating agent.

15. The method of claim 4, wherein the daily dosage is an aqueous ophthalmic solution free of a chelating agent, comprising:
(a) about 0.5% (w/v) to about 1% (w/v) of phentolamine mesylate;
(b) about 4% mannitol;
(c) about 3 mM sodium acetate; and
(d) water;
wherein the solution has a pH in the range of 4.6 to 5.2 and does not contain a chelating agent.

16. The method of claim 3, wherein the daily dosage is administered within 1 hour of the patient's bedtime.

17. The method of claim 12, wherein the daily dosage is administered within 1 hour of the patient's bedtime.

18. The method of claim 14, wherein the daily dosage is administered within 1 hour of the patient's bedtime.

19. The method of claim 15, wherein the daily dosage is administered within 1 hour of the patient's bedtime.

20. The method of claim 7, wherein the daily dosage is an aqueous ophthalmic solution free of a chelating agent, comprising:
(a) about 0.5% (w/v) to about 2% (w/v) of phentolamine mesylate;

(b) about 1% (w/v) to about 6% (w/v) of at least one polyol compound selected from the group consisting of is mannitol, glycerol, and propylene glycol;
(c) about 1 mM to about 6 mM of an alkali metal acetate; and
(d) water;

wherein the solution has a pH in the range of 4.5 to 5.5 and does not contain a chelating agent.

21. The method of claim 7, wherein the daily dosage is an aqueous ophthalmic solution free of a chelating agent, comprising:
    (a) about 0.5% (w/v) to about 2% (w/v) of phentolamine mesylate;
    (b) about 3% (w/v) to about 5% (w/v) of mannitol;
    (c) about 2 mM to about 4 mM of sodium acetate; and
    (d) water;

wherein the solution has a pH in the range of 4.6 to 5.2 and does not contain a chelating agent.

22. The method of claim 7, wherein the daily dosage is an aqueous ophthalmic solution free of a chelating agent, comprising:
    (a) about 0.5% (w/v) to about 1% (w/v) of phentolamine mesylate;
    (b) about 4% mannitol;
    (c) about 3 mM sodium acetate; and
    (d) water;

wherein the solution has a pH in the range of 4.6 to 5.2 and does not contain a chelating agent.

23. The method of claim 8, wherein the daily dosage is an aqueous ophthalmic solution free of a chelating agent, comprising:
    (a) about 0.5% (w/v) to about 1% (w/v) of phentolamine mesylate;
    (b) about 4% mannitol;
    (c) about 3 mM sodium acetate; and
    (d) water;

wherein the solution has a pH in the range of 4.6 to 5.2 and does not contain a chelating agent.

24. The method of claim 7, wherein the daily dosage is administered within 1 hour of the patient's bedtime.

25. The method of claim 20, wherein the daily dosage is administered within 1 hour of the patient's bedtime.

26. The method of claim 23, wherein the daily dosage is administered within 1 hour of the patient's bedtime.

* * * * *